US011109920B2

(12) United States Patent
Al-Jadda et al.

(10) Patent No.: US 11,109,920 B2
(45) Date of Patent: Sep. 7, 2021

(54) MEDICAL INSTRUMENTS WITH VARIABLE BENDING STIFFNESS PROFILES

(71) Applicant: Auris Health, Inc., Redwood City, CA (US)

(72) Inventors: Aadel Al-Jadda, San Carlos, CA (US); Curtis James Caton, San Jose, CA (US); Christopher Andrew Cook, Laguna Niguel, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/280,300

(22) Filed: Feb. 20, 2019

(65) Prior Publication Data

US 2019/0298460 A1    Oct. 3, 2019

Related U.S. Application Data

(60) Provisional application No. 62/649,460, filed on Mar. 28, 2018.

(51) Int. Cl.
*A61B 1/00* (2006.01)
*A61B 1/005* (2006.01)
*A61B 34/30* (2016.01)
*A61L 29/02* (2006.01)
*A61M 25/00* (2006.01)

(52) U.S. Cl.
CPC ............ *A61B 34/30* (2016.02); *A61B 1/0055* (2013.01); *A61B 1/0057* (2013.01); *A61B 1/00149* (2013.01); *A61L 29/02* (2013.01); *A61B 2034/301* (2016.02); *A61L 2400/16* (2013.01); *A61M 25/0054* (2013.01)

(58) Field of Classification Search
CPC .............. A61B 1/0055; A61B 1/00071; A61B 1/000154; A61B 1/00133; A61B 1/0016
USPC .......................... 600/114–115, 121–125, 144
See application file for complete search history.

(56) References Cited

U.S. PATENT DOCUMENTS 3,572,325 A    3/1971 Bazell et al.
3,913,565 A   10/1975 Kawahara
(Continued)

FOREIGN PATENT DOCUMENTS

CN    1846181    10/2006
CN    1857877    11/2006
(Continued)

OTHER PUBLICATIONS

International search report and written opinion dated Jul. 10, 2019 for PCT/US2019/18819.

*Primary Examiner* — Matthew J Kasztejna
(74) *Attorney, Agent, or Firm* — Morgan, Lewis & Bockius LLP

(57) ABSTRACT

Medical instruments with variable bending stiffness profiles are disclosed. A medical instrument can include a bending stiffness profile comprising a plurality of bending stiffness zones of substantially constant bending stiffness separated by transition zones. The bending stiffness profile can be achieved by modulating various modalities of the medical instrument along its length. A compound medical instrument can include a scope telescoping within a sheath. A variable bending stiffness profile of the compound medical instrument can be modulated by adjusting the relative position of the scope and the sheath.

23 Claims, 29 Drawing Sheets

(56) References Cited

U.S. PATENT DOCUMENTS

| | | | |
|---|---|---|---|
| 4,294,234 A | 10/1981 | Matsuo | |
| 4,392,485 A | 7/1983 | Hiltebrandt | |
| 4,607,619 A | 8/1986 | Seike et al. | |
| 4,690,175 A * | 9/1987 | Ouchi | A61B 1/0055 |
| | | | 138/131 |
| 4,706,656 A | 11/1987 | Kubota | |
| 4,741,326 A | 5/1988 | Sidall et al. | |
| 4,745,908 A | 5/1988 | Wardle | |
| 4,748,969 A | 6/1988 | Wardle | |
| 4,750,475 A | 6/1988 | Yoshihashi | |
| 4,771,766 A | 9/1988 | Aoshiro | |
| 4,846,791 A | 7/1989 | Hattler et al. | |
| 4,869,238 A | 9/1989 | Opie et al. | |
| 4,906,496 A | 3/1990 | Hosono et al. | |
| 4,907,168 A | 3/1990 | Boggs | |
| 4,967,732 A | 11/1990 | Inoue | |
| 5,050,585 A | 9/1991 | Takahashi | |
| 5,083,549 A * | 1/1992 | Cho | A61B 1/00071 |
| | | | 600/108 |
| 5,106,387 A | 4/1992 | Kittrell et al. | |
| 5,108,800 A | 4/1992 | Koo | |
| 5,125,909 A | 6/1992 | Heimberger | |
| 5,168,864 A | 12/1992 | Shockey | |
| 5,217,002 A * | 6/1993 | Katsurada | A61B 1/00071 |
| | | | 600/139 |
| 5,251,611 A * | 10/1993 | Zehel | A61B 1/0055 |
| | | | 600/114 |
| 5,257,617 A | 11/1993 | Takahashi | |
| 5,261,391 A | 11/1993 | Inoue | |
| 5,287,861 A | 2/1994 | Wilk | |
| 5,313,934 A | 5/1994 | Wiita et al. | |
| 5,386,818 A | 2/1995 | Schneebaum | |
| 5,448,988 A * | 9/1995 | Watanabe | A61B 1/0055 |
| | | | 138/118 |
| 5,478,330 A | 12/1995 | Imran et al. | |
| 5,482,029 A * | 1/1996 | Sekiguchi | A61B 1/00039 |
| | | | 600/109 |
| 5,489,270 A | 2/1996 | van Erp | |
| 5,507,725 A | 4/1996 | Savage et al. | |
| 5,533,985 A * | 7/1996 | Wang | A61M 25/0009 |
| | | | 604/264 |
| 5,580,200 A | 12/1996 | Fullerton | |
| 5,681,296 A | 10/1997 | Ishida | |
| 5,704,534 A | 1/1998 | Huitema et al. | |
| 5,720,775 A | 2/1998 | Lamard | |
| 5,741,429 A * | 4/1998 | Donadio, III | A61M 25/0043 |
| | | | 216/10 |
| 5,749,889 A | 5/1998 | Bacich et al. | |
| 5,873,817 A | 2/1999 | Kokish et al. | |
| 5,876,325 A | 3/1999 | Mizuno et al. | |
| 5,879,287 A | 3/1999 | Yoshihashi | |
| 5,882,347 A | 3/1999 | Mouris-Laan | |
| 5,888,191 A | 3/1999 | Akiba | |
| 5,910,129 A | 6/1999 | Koblish et al. | |
| 5,938,586 A | 8/1999 | Wilk | |
| 5,938,587 A | 8/1999 | Taylor et al. | |
| 6,012,494 A * | 1/2000 | Balazs | B25J 18/06 |
| | | | 138/110 |
| 6,143,013 A | 11/2000 | Samson et al. | |
| 6,157,853 A | 12/2000 | Blume et al. | |
| 6,174,280 B1 * | 1/2001 | Oneda | A61B 1/00078 |
| | | | 600/114 |
| 6,197,015 B1 * | 3/2001 | Wilson | A61M 25/005 |
| | | | 156/158 |
| 6,198,974 B1 | 3/2001 | Webster, Jr. | |
| 6,234,958 B1 | 5/2001 | Snoke et al. | |
| 6,315,715 B1 | 11/2001 | Taylor et al. | |
| 6,404,497 B1 | 6/2002 | Backman | |
| 6,436,107 B1 | 8/2002 | Wang et al. | |
| 6,464,632 B1 | 10/2002 | Taylor | |
| 6,485,411 B1 * | 11/2002 | Konstorum | A61B 1/0058 |
| | | | 600/139 |
| 6,491,626 B1 | 12/2002 | Stone et al. | |
| 6,537,205 B1 | 3/2003 | Smith | |
| 6,554,793 B1 | 4/2003 | Pauker et al. | |
| 6,716,178 B1 | 4/2004 | Kilpatrick et al. | |
| 6,746,422 B1 * | 6/2004 | Noriega | A61M 25/0138 |
| | | | 604/95.05 |
| 6,749,560 B1 * | 6/2004 | Konstorum | A61B 1/00071 |
| | | | 600/139 |
| 6,790,173 B2 * | 9/2004 | Saadat | A61B 1/0008 |
| | | | 600/114 |
| 6,827,710 B1 | 12/2004 | Mooney et al. | |
| 6,827,712 B2 | 12/2004 | Tovey et al. | |
| 6,837,846 B2 * | 1/2005 | Jaffe | A61B 1/0008 |
| | | | 600/114 |
| 6,908,428 B2 | 6/2005 | Aizenfeld | |
| 6,921,362 B2 | 7/2005 | Ouchi | |
| 6,958,035 B2 | 10/2005 | Friedman et al. | |
| 7,008,401 B2 | 3/2006 | Thompson et al. | |
| 7,130,700 B2 | 10/2006 | Gardeski et al. | |
| 7,594,903 B2 | 9/2009 | Webler et al. | |
| 7,645,230 B2 | 1/2010 | Mikkaichi | |
| 7,645,231 B2 | 1/2010 | Akiba | |
| 7,781,724 B2 | 8/2010 | Childers et al. | |
| 7,789,827 B2 * | 9/2010 | Landry | A61B 1/00071 |
| | | | 600/140 |
| 7,930,065 B2 | 4/2011 | Larkin et al. | |
| 8,046,049 B2 | 10/2011 | Govari et al. | |
| 8,052,636 B2 | 11/2011 | Moll et al. | |
| 8,246,536 B2 | 8/2012 | Ochi | |
| 8,444,637 B2 | 5/2013 | Podmore et al. | |
| 8,460,236 B2 | 6/2013 | Roelle et al. | |
| 8,498,691 B2 | 7/2013 | Moll et al. | |
| 8,515,215 B2 | 8/2013 | Younge et al. | |
| 8,652,030 B2 | 2/2014 | Matsuura et al. | |
| 8,686,747 B2 | 4/2014 | Berner | |
| 8,758,231 B2 | 6/2014 | Bunch et al. | |
| 8,827,947 B2 | 9/2014 | Bosman et al. | |
| 9,186,046 B2 | 11/2015 | Ramamurthy et al. | |
| 9,314,953 B2 * | 4/2016 | Lauer | B29D 99/0096 |
| 9,427,551 B2 | 8/2016 | Leeflang et al. | |
| 9,504,604 B2 | 11/2016 | Alvarez | |
| 9,561,083 B2 | 2/2017 | Yu et al. | |
| 9,591,990 B2 | 3/2017 | Chen et al. | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,726,476 B2 | 8/2017 | Ramamurthy et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,814,373 B2 * | 11/2017 | Saito | A61B 1/0055 |
| 9,844,353 B2 | 12/2017 | Walker et al. | |
| 9,844,412 B2 | 12/2017 | Bogusky et al. | |
| 9,867,635 B2 | 1/2018 | Alvarez et al. | |
| 9,918,659 B2 | 3/2018 | Chopra | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,016,900 B1 | 7/2018 | Meyer et al. | |
| 10,022,192 B1 | 7/2018 | Ummalaneni | |
| 10,080,576 B2 | 9/2018 | Romo et al. | |
| 10,130,427 B2 | 11/2018 | Tanner et al. | |
| 10,136,959 B2 | 11/2018 | Mintz et al. | |
| 10,143,526 B2 | 12/2018 | Walker et al. | |
| 10,145,747 B1 | 12/2018 | Lin et al. | |
| 10,149,720 B2 | 12/2018 | Romo | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,219,874 B2 | 3/2019 | Yu et al. | |
| 10,231,793 B2 | 3/2019 | Romo | |
| 10,231,867 B2 | 3/2019 | Alvarez et al. | |
| 10,314,463 B2 | 6/2019 | Agrawal et al. | |
| 10,405,908 B2 | 9/2019 | Redmond et al. | |

(56) References Cited

U.S. PATENT DOCUMENTS

| | | | |
|---|---|---|---|
| 10,524,866 B2 | 1/2020 | Srinivasan | |
| 10,820,954 B2 | 11/2020 | Marsot et al. | |
| 2001/0004676 A1 | 6/2001 | Ouchi | |
| 2003/0036748 A1 | 2/2003 | Cooper et al. | |
| 2003/0130564 A1 | 7/2003 | Martone et al. | |
| 2003/0158545 A1 | 8/2003 | Hovda et al. | |
| 2003/0163199 A1 | 8/2003 | Chu et al. | |
| 2003/0195664 A1 | 10/2003 | Nowlin et al. | |
| 2004/0015122 A1 | 1/2004 | Zhang et al. | |
| 2004/0054322 A1* | 3/2004 | Vargas | A61M 25/00 604/95.04 |
| 2004/0072066 A1 | 4/2004 | Cho et al. | |
| 2004/0138525 A1 | 7/2004 | Saadat et al. | |
| 2004/0193013 A1 | 9/2004 | Iwasaka et al. | |
| 2004/0249246 A1* | 12/2004 | Campos | A61B 1/0008 600/160 |
| 2005/0004515 A1 | 1/2005 | Hart et al. | |
| 2005/0125005 A1 | 6/2005 | Fujikura | |
| 2005/0131279 A1 | 6/2005 | Boulais et al. | |
| 2005/0154262 A1 | 7/2005 | Banik et al. | |
| 2005/0159646 A1 | 7/2005 | Nordstrom et al. | |
| 2005/0165366 A1* | 7/2005 | Brustad | A61B 1/0055 604/264 |
| 2005/0222581 A1 | 10/2005 | Fischer et al. | |
| 2005/0234293 A1* | 10/2005 | Yamamoto | A61B 90/57 600/102 |
| 2005/0256452 A1* | 11/2005 | DeMarchi | A61M 25/0017 604/95.04 |
| 2005/0272975 A1 | 12/2005 | McWeeney et al. | |
| 2005/0273085 A1 | 12/2005 | Hinman et al. | |
| 2005/0288549 A1 | 12/2005 | Mathis | |
| 2006/0041188 A1 | 2/2006 | Dirusso et al. | |
| 2006/0111692 A1 | 5/2006 | Hlavka et al. | |
| 2006/0241368 A1 | 10/2006 | Fichtinger et al. | |
| 2006/0264708 A1 | 11/2006 | Horne | |
| 2006/0276827 A1 | 12/2006 | Mitelberg et al. | |
| 2007/0060879 A1 | 3/2007 | Weitzner et al. | |
| 2007/0112355 A1 | 5/2007 | Salahieh | |
| 2007/0135733 A1 | 6/2007 | Soukup et al. | |
| 2007/0135763 A1 | 6/2007 | Musbach et al. | |
| 2007/0135803 A1 | 6/2007 | Belson | |
| 2007/0156019 A1 | 7/2007 | Larkin et al. | |
| 2007/0270645 A1 | 11/2007 | Ikeda | |
| 2007/0270679 A1 | 11/2007 | Nguyen et al. | |
| 2007/0282167 A1 | 12/2007 | Barenboym et al. | |
| 2007/0287886 A1 | 12/2007 | Saadat | |
| 2008/0039255 A1 | 2/2008 | Jinno et al. | |
| 2008/0051629 A1 | 2/2008 | Sugiyama et al. | |
| 2008/0065103 A1 | 3/2008 | Cooper et al. | |
| 2008/0097293 A1 | 4/2008 | Chin et al. | |
| 2008/0108869 A1 | 5/2008 | Sanders et al. | |
| 2008/0139887 A1 | 6/2008 | Fitpatrick | |
| 2008/0146874 A1 | 6/2008 | Miller | |
| 2008/0147089 A1 | 6/2008 | Loh | |
| 2008/0177285 A1 | 7/2008 | Brock et al. | |
| 2008/0208001 A1 | 8/2008 | Hadani | |
| 2008/0212082 A1 | 9/2008 | Froggatt et al. | |
| 2008/0218770 A1 | 9/2008 | Moll et al. | |
| 2009/0099420 A1 | 4/2009 | Woodley et al. | |
| 2009/0163851 A1 | 6/2009 | Holloway | |
| 2009/0247880 A1 | 10/2009 | Naruse et al. | |
| 2009/0254083 A1 | 10/2009 | Wallace et al. | |
| 2009/0262109 A1 | 10/2009 | Markowitz et al. | |
| 2009/0299344 A1 | 12/2009 | Lee et al. | |
| 2009/0306587 A1 | 12/2009 | Milijasevic et al. | |
| 2010/0030023 A1 | 2/2010 | Yoshie | |
| 2010/0073150 A1 | 3/2010 | Olson et al. | |
| 2010/0114115 A1 | 5/2010 | Schlesinger et al. | |
| 2010/0130823 A1 | 5/2010 | Ando | |
| 2010/0168918 A1 | 7/2010 | Zhao | |
| 2010/0217184 A1 | 8/2010 | Koblish et al. | |
| 2010/0234831 A1 | 9/2010 | Hinman et al. | |
| 2010/0249497 A1 | 9/2010 | Peine et al. | |
| 2010/0249506 A1 | 9/2010 | Prisco et al. | |
| 2011/0009863 A1 | 1/2011 | Stanislaw | |
| 2011/0046441 A1 | 2/2011 | Wiltshire et al. | |
| 2011/0077681 A1 | 3/2011 | Nagano | |
| 2011/0098533 A1 | 4/2011 | Onoda | |
| 2011/0130718 A1 | 6/2011 | Kidd et al. | |
| 2011/0148442 A1 | 6/2011 | Berner | |
| 2011/0152880 A1 | 6/2011 | Alvarez et al. | |
| 2011/0245844 A1 | 10/2011 | Jinno et al. | |
| 2011/0261183 A1 | 10/2011 | Ma et al. | |
| 2011/0306836 A1 | 12/2011 | Ohline et al. | |
| 2012/0071894 A1 | 3/2012 | Tanner et al. | |
| 2012/0071895 A1 | 3/2012 | Stahler et al. | |
| 2012/0123327 A1 | 5/2012 | Miller | |
| 2012/0136419 A1 | 5/2012 | Zarembo et al. | |
| 2012/0143226 A1 | 6/2012 | Belson et al. | |
| 2012/0190976 A1 | 7/2012 | Kleinstreuer | |
| 2012/0191107 A1 | 7/2012 | Tanner et al. | |
| 2012/0239012 A1 | 9/2012 | Laurent et al. | |
| 2012/0259244 A1 | 10/2012 | Roberts et al. | |
| 2012/0283747 A1 | 11/2012 | Popovic | |
| 2012/0289777 A1 | 11/2012 | Chopra | |
| 2013/0018400 A1 | 1/2013 | Milton et al. | |
| 2013/0030519 A1 | 1/2013 | Tran et al. | |
| 2013/0035537 A1 | 2/2013 | Wallace et al. | |
| 2013/0090552 A1 | 4/2013 | Ramamurthy et al. | |
| 2013/0109957 A1 | 5/2013 | Hooft et al. | |
| 2013/0144116 A1 | 6/2013 | Cooper et al. | |
| 2013/0165854 A1 | 6/2013 | Sandhu et al. | |
| 2013/0165908 A1 | 6/2013 | Purdy et al. | |
| 2013/0204124 A1 | 8/2013 | Duindam | |
| 2013/0226151 A1 | 8/2013 | Suehara | |
| 2013/0303892 A1 | 11/2013 | Zhao | |
| 2013/0304091 A1 | 11/2013 | Straehnz | |
| 2013/0317276 A1 | 11/2013 | D'Andrea | |
| 2013/0317519 A1 | 11/2013 | Romo et al. | |
| 2013/0345519 A1 | 12/2013 | Piskun et al. | |
| 2014/0012288 A1* | 1/2014 | Darisse | A61B 1/0055 606/130 |
| 2014/0046313 A1 | 2/2014 | Pederson et al. | |
| 2014/0142591 A1 | 5/2014 | Alvarez et al. | |
| 2014/0200402 A1 | 7/2014 | Snoke et al. | |
| 2014/0235943 A1 | 8/2014 | Paris | |
| 2014/0276391 A1 | 9/2014 | Yu | |
| 2014/0276594 A1 | 9/2014 | Tanner et al. | |
| 2014/0316397 A1 | 10/2014 | Brown | |
| 2014/0343416 A1 | 11/2014 | Panescu | |
| 2014/0357984 A1 | 12/2014 | Wallace et al. | |
| 2014/0364870 A1 | 12/2014 | Alvarez et al. | |
| 2015/0031950 A1 | 1/2015 | Drontle et al. | |
| 2015/0051592 A1 | 2/2015 | Kintz | |
| 2015/0164594 A1 | 6/2015 | Romo et al. | |
| 2015/0164596 A1 | 6/2015 | Romo | |
| 2015/0255782 A1 | 9/2015 | Kim et al. | |
| 2015/0335480 A1 | 11/2015 | Alvarez et al. | |
| 2016/0000414 A1 | 1/2016 | Brown | |
| 2016/0001038 A1 | 1/2016 | Romo et al. | |
| 2016/0007881 A1 | 1/2016 | Wong et al. | |
| 2016/0067450 A1 | 3/2016 | Kowshik | |
| 2016/0151122 A1 | 6/2016 | Alvarez et al. | |
| 2016/0183841 A1 | 6/2016 | Duindam et al. | |
| 2016/0227982 A1 | 8/2016 | Takahashi | |
| 2016/0270865 A1 | 9/2016 | Landey et al. | |
| 2016/0287279 A1 | 10/2016 | Bovay et al. | |
| 2016/0287346 A1 | 10/2016 | Hyodo et al. | |
| 2016/0346049 A1 | 12/2016 | Allen et al. | |
| 2016/0372743 A1 | 12/2016 | Cho et al. | |
| 2016/0374541 A1 | 12/2016 | Agrawal et al. | |
| 2016/0374590 A1 | 12/2016 | Wong et al. | |
| 2017/0007337 A1 | 1/2017 | Dan | |
| 2017/0100199 A1 | 4/2017 | Yu et al. | |
| 2017/0119481 A1 | 5/2017 | Romo et al. | |
| 2017/0165011 A1 | 6/2017 | Bovay et al. | |
| 2017/0172673 A1 | 6/2017 | Yu et al. | |
| 2017/0202627 A1 | 7/2017 | Sramek et al. | |
| 2017/0209073 A1 | 7/2017 | Sramek et al. | |
| 2017/0281218 A1 | 10/2017 | Timm | |
| 2017/0290631 A1 | 10/2017 | Lee et al. | |
| 2017/0333679 A1 | 11/2017 | Jiang | |
| 2017/0340396 A1 | 11/2017 | Romo et al. | |

(56) References Cited

U.S. PATENT DOCUMENTS

| | | |
|---|---|---|
| 2017/0367782 A1 | 12/2017 | Schuh et al. |
| 2018/0025666 A1 | 1/2018 | Ho et al. |
| 2018/0055589 A1 | 3/2018 | Joseph et al. |
| 2018/0177383 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105110 A1 | 4/2019 | Tanner et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298465 A1 | 10/2019 | Chin |
| 2019/0307987 A1 | 10/2019 | Yu |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0038123 A1 | 2/2020 | Graetzel |
| 2020/0038128 A1 | 2/2020 | Joseph |
| 2020/0039086 A1 | 2/2020 | Meyer |
| 2020/0046434 A1 | 2/2020 | Graetzel |
| 2020/0046942 A1 | 2/2020 | Alvarez |
| 2020/0054405 A1 | 2/2020 | Schuh |
| 2020/0054408 A1 | 2/2020 | Schuh et al. |
| 2020/0060516 A1 | 2/2020 | Baez |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0337593 A1 | 10/2020 | Wong |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |

FOREIGN PATENT DOCUMENTS

| | | |
|---|---|---|
| CN | 102316817 | 1/2012 |
| CN | 102458295 | 5/2012 |
| CN | 102665590 | 9/2012 |
| CN | 102711586 | 10/2012 |
| CN | 102973317 | 3/2013 |
| CN | 103767659 | 5/2014 |
| CN | 103930063 | 7/2014 |
| EP | 0 543 539 | 5/1993 |
| EP | 0 776 739 | 6/1997 |
| EP | 1 442 720 | 8/2004 |
| EP | 0 904 796 | 11/2004 |
| JP | 2006-525087 | 11/2006 |
| JP | 2007-511247 | 5/2007 |
| JP | 2010-046384 | 3/2010 |
| JP | 2011-015992 | 1/2011 |
| JP | 2012-105793 | 6/2012 |
| WO | WO 94/14494 | 7/1994 |
| WO | WO 00/67640 | 11/2000 |
| WO | WO 02/74178 | 9/2002 |
| WO | WO 04/039273 | 5/2004 |
| WO | WO 04/105849 | 12/2004 |
| WO | WO 05/032637 | 4/2005 |
| WO | WO 05/081202 | 9/2005 |
| WO | WO 09/097461 | 6/2007 |
| WO | WO 07/146987 | 12/2007 |
| WO | WO 08/097540 | 8/2008 |
| WO | WO 09/092059 | 7/2009 |
| WO | WO 10/081187 | 7/2010 |
| WO | WO 11/005335 | 1/2011 |
| WO | WO 13/107468 | 7/2013 |
| WO | WO 15/093602 | 12/2013 |
| WO | WO 16/003052 | 1/2016 |

\* cited by examiner

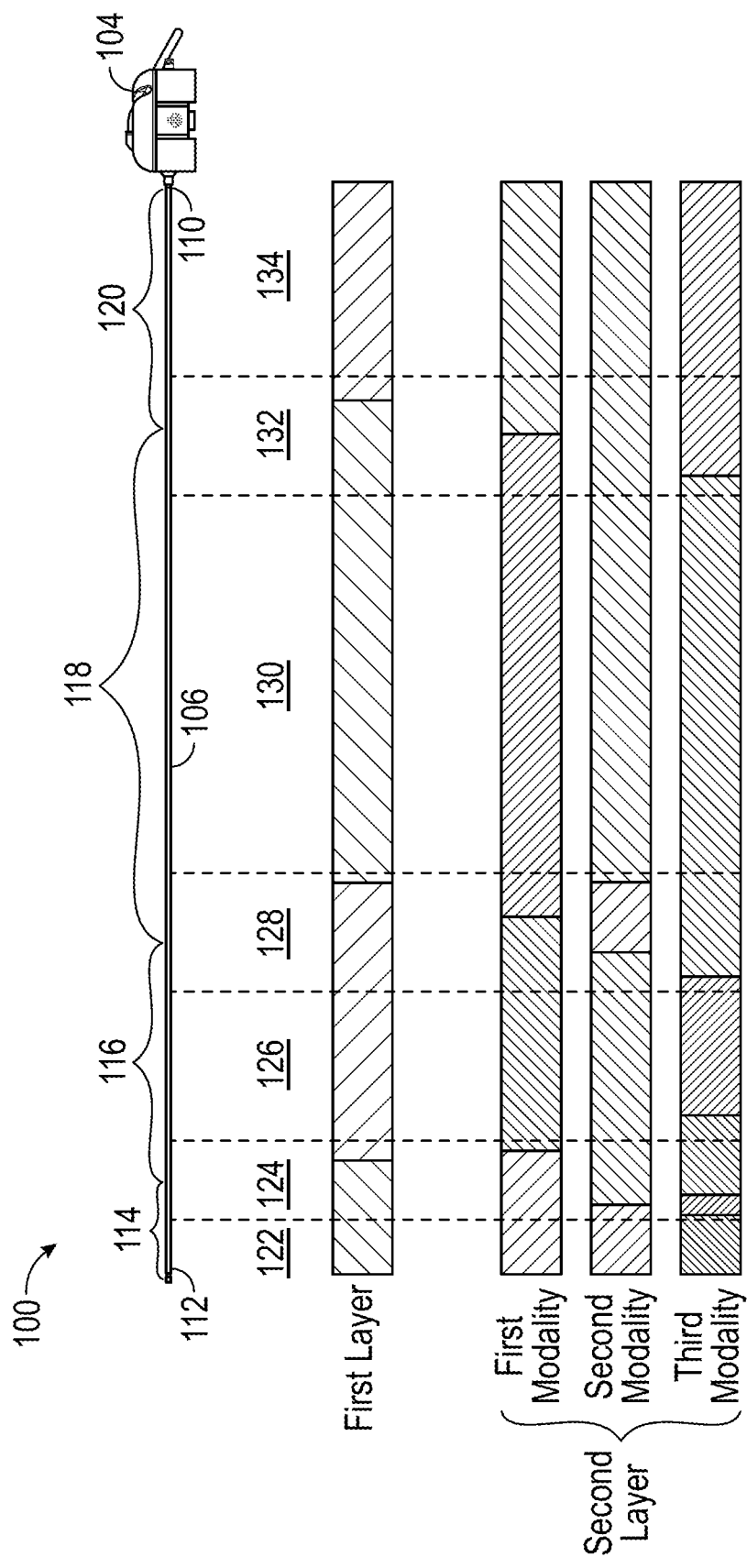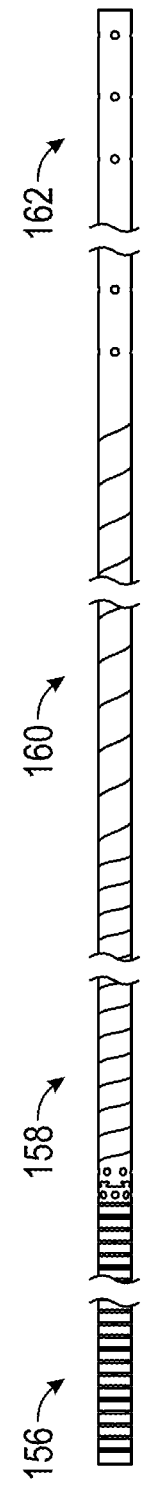

MEDICAL INSTRUMENTS WITH VARIABLE BENDING STIFFNESS PROFILES

INCORPORATION BY REFERENCE TO ANY PRIORITY APPLICATIONS

This application claims priority to U.S. Provisional Application No. 62/649,460, filed Mar. 28, 2018, which is incorporated herein by reference. Any and all applications for which a foreign or domestic priority claim is identified in the Application Data Sheet as filed with the present application are hereby incorporated by reference under 37 CFR 1.57.

TECHNICAL FIELD

This application relates to medical instruments. More particularly, this application relates to medical instruments with variable bending stiffness profiles.

BACKGROUND

Medical procedures such as endoscopy (e.g., bronchoscopy) may involve accessing and visualizing the inside of a patient's lumen(s) (e.g., airways) for diagnostic and/or therapeutic purposes.

Bronchoscopy is a medical procedure that allows a physician to examine airways in a patient's lungs, such as bronchi and bronchioles. During the procedure, a thin, flexible tubular tool or instrument, known as a bronchoscope, is inserted into the patient's mouth and passed down the patient's throat into his or her lung airways towards a tissue site identified for subsequent diagnosis and/or treatment.

In certain procedures, a robotically-enabled medical system may be used to control the insertion and/or manipulation of the instrument. The robotically-enabled medical system may include a robotic arm, or other instrument positioning device, having a manipulator assembly used to control the positioning of the instrument during the procedure.

SUMMARY

In a first aspect, a medical instrument is described. The medical instrument includes an elongated shaft extending between a distal end and a proximal end. The elongated shaft includes at least three bending stiffness zones arranged along a length of the elongated shaft, each bending stiffness zone comprising a bending stiffness that extends over a length of the bending stiffness zone, wherein the bending stiffness of each of the bending stiffness zones is greater or less than the bending stiffness of an adjacent bending stiffness zone, and wherein the bending stiffness of each of the bending stiffness zones is substantially uniform along its length. The elongated shaft also includes at least two transition zones, wherein each transition zone comprises a variable bending stiffness extending a length between each pair of the at least three bending stiffness zones, wherein the variable bending stiffness for each transition zone varies from a first bending stiffness on a first side of the transition zone to a second bending stiffness on a second side of the transition zone.

The medical instrument can also include one or more of the following features in any combination: (a) wherein, for each transition zone, the variable bending stiffness varies from the first bending stiffness on the first side of the transition zone to the second bending stiffness on the second side of the transition zone with a substantially linear slope; (b) wherein the bending stiffness zone closest to the distal end has a bending stiffness that is less than each of the three other bending stiffness zones; (c) wherein the bending stiffness zone closest to the proximal end has a bending stiffness that is greater than each of the three other bending stiffness zones; (d) wherein, from the proximal end to the distal end, the bending stiffness of each of the at least four bending stiffness zones increases; (e) wherein each of the bending stiffness zones has a minimum length of at least 50 mm; (f) wherein each of the transition zones has a minimum length of at least 10 mm; (g) wherein the elongate shaft comprises an inner layer and an outer layer; (h) wherein the outer layer comprises a braided jacket and the inner layer comprises an endoskeleton; (i) wherein the braided jacket comprises one or more pull wires extending therethrough; (j) wherein the bending stiffness of the braided jacket can be modulated by at least one of the following: jacket material durometer, braid geometry, and braid pic count; (k) wherein the endoskeleton comprises a first portion formed of nitinol and a second portion formed of stainless steel; (l) wherein the second portion formed comprises a first section with coils having at least a first pitch and a second section with coils having at least a second pitch; (m) wherein the second portion formed by stainless steel further comprises a third section formed as a rigid hypotube; (n) wherein the medical instrument comprises an endoscope; (o) wherein the elongate shaft has a bending stiffness profile that is omnidirectional; (p) wherein the elongate shaft has a bending stiffness profile that is stepped; and/or (q) wherein each of the transition zones has a bending stiffness in the form of a gradual slope.

In another aspect, a medical system is described. The medical system includes an elongated member having a length extending between a distal end and a proximal end, the elongated member further comprising n bending stiffness zones of different bending stiffnesses, wherein each of the n bending stiffness zones has a bending stiffness that is substantially uniform along its length. The system also includes a sheath having a sheath length extending between a sheath distal end and a sheath proximal end, the sheath comprising an inner channel. The elongated member is moveable within the inner channel of the sheath such that the elongated member and the sheath form a compound structure having at least n+1 bending stiffness zones, wherein each of the n+1 bending stiffness zones has a bending stiffness that is substantially uniform along its length.

In some embodiments, the system can include one or more of the following features in any combination: (a) wherein the compound structure comprises at least n+1 bending stiffness zones when the scope is advanced through the sheath such that the scope distal end is positioned distally of the sheath distal end; (b) wherein the sheath comprises at least n bending stiffness zones of different bending stiffnesses, wherein each of the n bending stiffness zones has a bending stiffness that is substantially uniform across its length, and wherein the scope can be positioned relative to the sheath such that the compound structure comprises at least 2n bending stiffness zones; (c) wherein the scope has four zones of bending stiffness and the compound structure has greater than four zones of bending stiffness; (d) wherein the scope and the sheath are of different lengths; (e) wherein the sheath comprises a plurality of zones of bending stiffness; (f) wherein the sheath comprises at least four zones of bending stiffness; and/or (g) a first robotic arm, the scope attached to the first robotic arm, and a second robotic arm, the sheath attached to the second robotic arm, wherein the first robotic arm is configured to advance or retract the scope relative to the sheath, and the second robotic arm is configured to advance or retract the sheath relative to the scope.

In another aspect, a method for navigating a medical instrument within a patient is described. The method includes: inserting the medical instrument into a patient lumen, wherein the medical instrument comprises: a scope comprising a plurality of bending stiffness zones arranged along a length of the scope, wherein each of the bending stiffness zones has a bending stiffness that is substantially uniform, and a sheath comprising a plurality of bending stiffness zones arranged along a length of the sheath, the sheath further comprising an inner channel, wherein the scope is positioned within the inner channel of the sheath; and modulating a bending stiffness profile of the medical instrument by adjusting the position of at least one of the scope and the sheath relative to the other of the scope and the sheath.

The method can include one or more of the following features in any combination: (a) wherein modulating the bending stiffness profile of the medical instrument comprises advancing the scope or retracting the sheath such that the scope extends distally from the sheath; (b) wherein modulating the bending stiffness profile of the medical instrument comprises advancing the sheath or retracting the scope such that a distal end of the scope is positioned within the inner channel of the sheath; (c) wherein a distal end of the sheath is positioned distally beyond the distal end of the scope; (d) wherein the distal end of the scope is aligned with a distal end of the sheath; (e) wherein the scope comprises at least four bending stiffness zones, each having a substantially constant bending stiffness a long a length of the zone; (f) wherein the scope comprises at least three zones, each positioned between a pair of the at least four bending stiffness zones; (g) wherein the scope comprises at least three bending stiffness zones, each having a substantially constant bending stiffness a long a length of the zone; (h) wherein the scope comprises at least two zones, each positioned between a pair of the at least four bending stiffness zones; (i) wherein the patient lumen comprises the bronchial airways; (j) wherein a first bending stiffness zone has a bending stiffness that is less relative to the other bending stiffness zones; (k) wherein a third zone of bending stiffness extends through an introducer; and/or (l) wherein a fourth zone of bending stiffness does not extend through the patient lumen, nor through the introducer.

In another aspect, a medical instrument is described. The medical instrument includes an elongated shaft extending between a distal end and a proximal end. The elongated shaft includes a first modality for modulating a bending stiffness of the elongated shaft, wherein a modality of the first modality changes at a first point between the distal end and the proximal end, and a second modality for modulating the bending stiffness of the elongated shaft, wherein a modality of the second modality changes at a second point between the distal end and the proximal end, the second point different than the first point. The first point and the second point are positioned such that a bending stiffness profile of the elongated shaft comprises a first bending stiffness zone having a first bending stiffness, a second bending stiffness zone having a second bending stiffness, and a transition zone positioned between the first bending stiffness zone and the second bending stiffness zone, the transition zone comprising a length over which a bending stiffness of the transition zone transitions from the first bending stiffness to the second bending stiffness.

The medical instrument can include one or more of the following features in any combination: (a) wherein the first modality is disposed in a first layer and the second modality is disposed in a second layer; (b) wherein the first modality and second modality are disposed in the same layer; (c) wherein the first modality comprises a material property; (d) wherein the material property comprises hardness; (e) wherein the second modality comprises a mechanical property; (f) wherein the mechanical property comprises at least one of braid geometry and braid pic count; and/or (g) a third modality for modulating bending stiffness.

In another aspect, a non-transitory computer readable medium storing instructions is described. The instructions are configured to cause a processor of a device to at least: insert a medical instrument into a patient lumen. The medical instrument comprises a scope comprising a plurality of bending stiffness zones arranged along a length of the scope, wherein each of the bending stiffness zones has a bending stiffness that is substantially uniform, and a sheath comprising a plurality of bending stiffness zones arranged along a length of the sheath, the sheath further comprising an inner channel, wherein the scope is positioned within the inner channel of the sheath. The instructions are configured to also cause the processor of the device to at least modulate a bending stiffness profile of the medical instrument by adjusting the position of at least one of the scope and the sheath relative to the other of the scope and the sheath.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 16D schematically illustrates an example of how individual modalities of the multi-modality construction can be varied to achieve the example variable bending stiffness profile of FIG. 16B for the medical instrument of FIG. 16A.

FIG. 17 illustrates a side view of one embodiment of an endoskeleton for a medical instrument with a variable bending stiffness profile.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
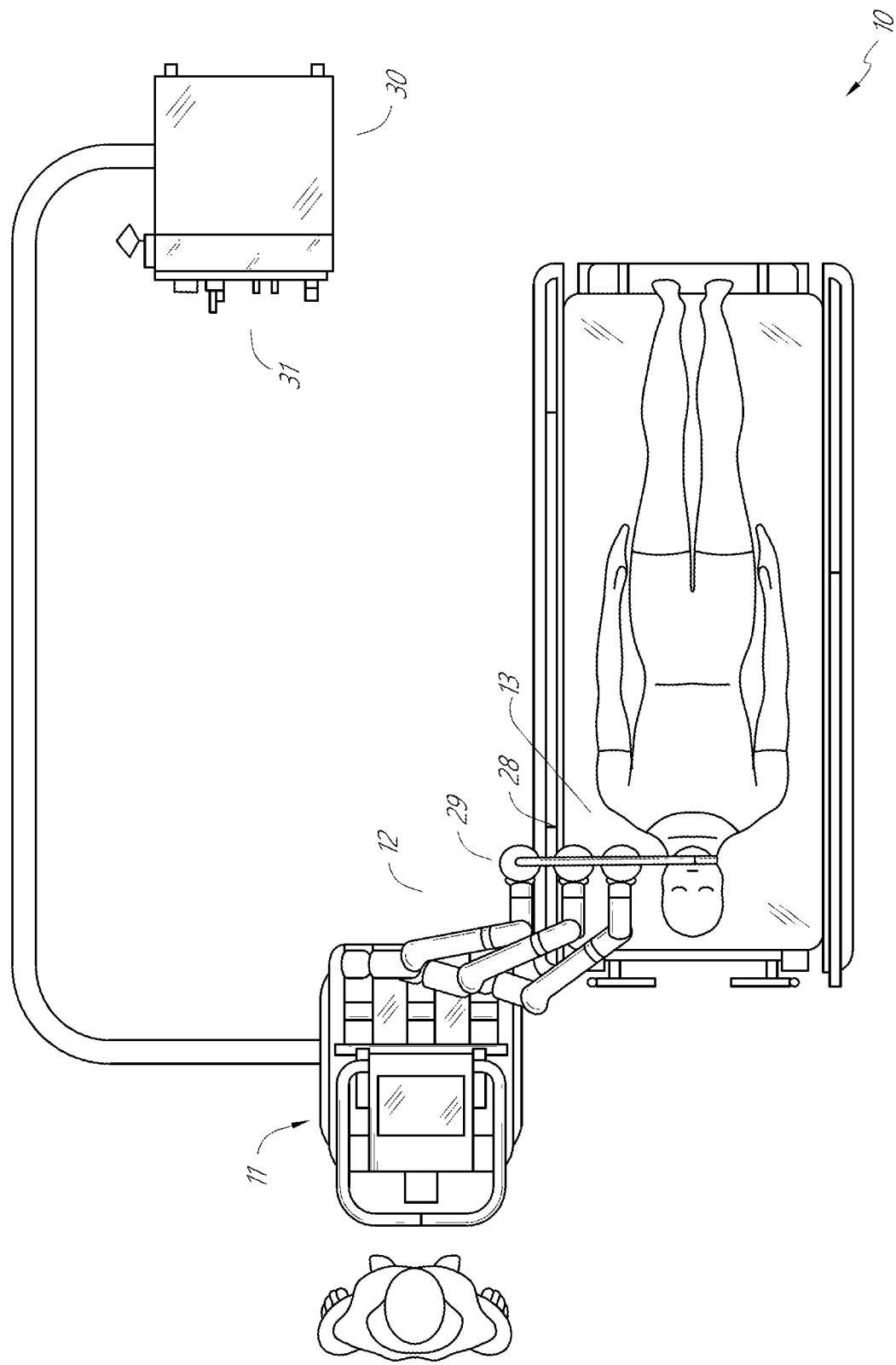
FIG. 1 illustrates an embodiment of a cart-based robotic system arranged for diagnostic and/or therapeutic bronchoscopy procedure(s).
Figure 2:
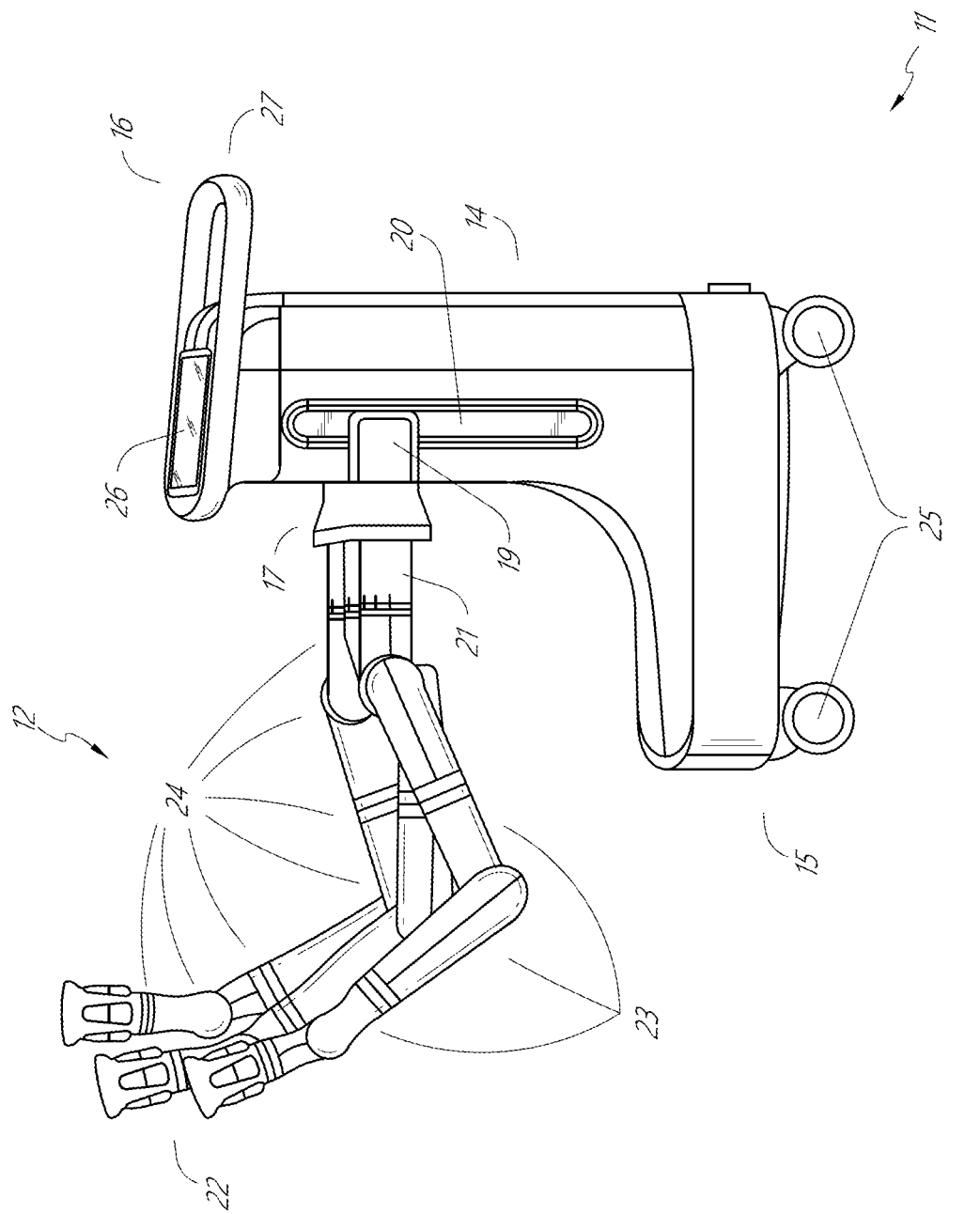
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
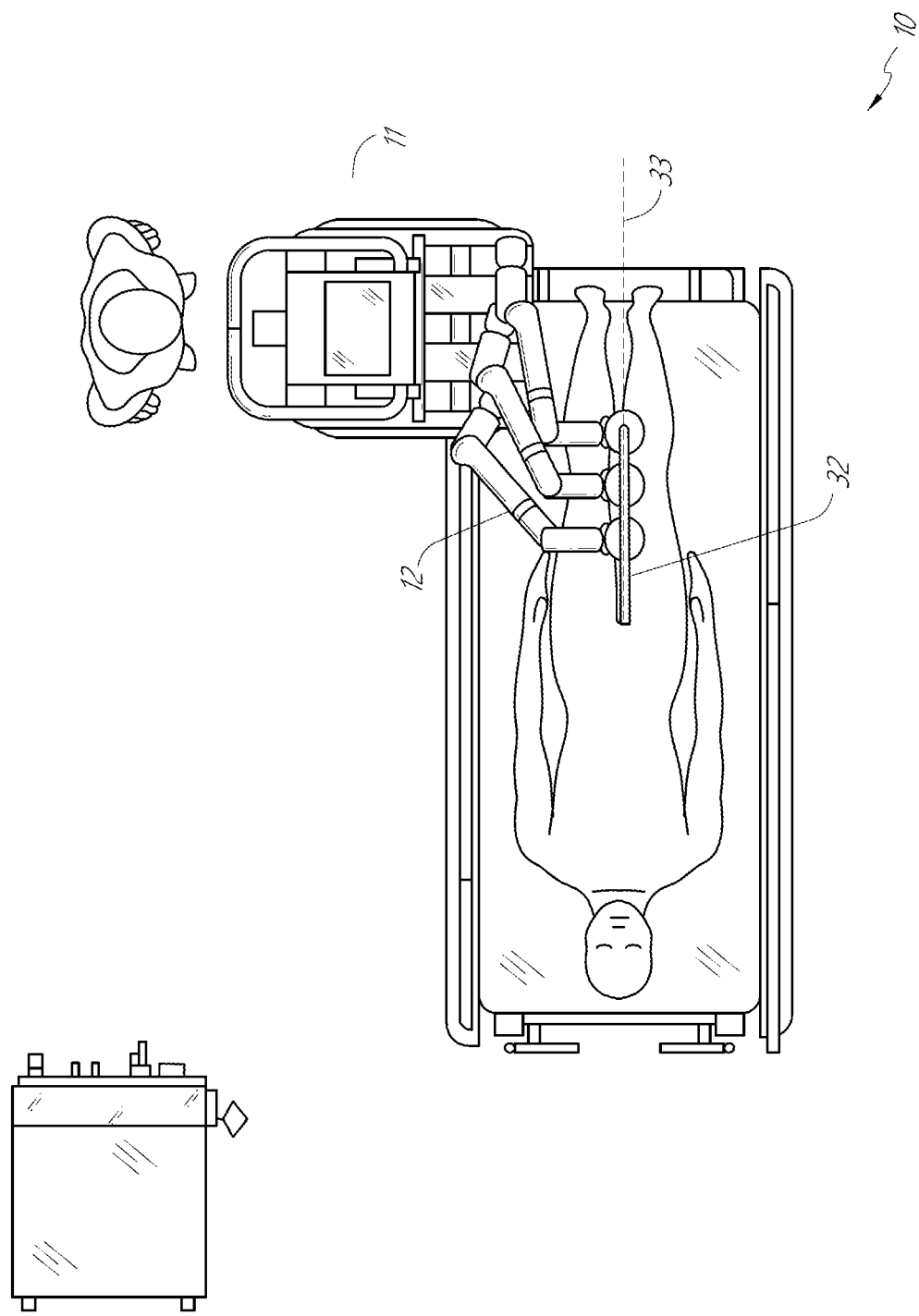
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may the insert ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
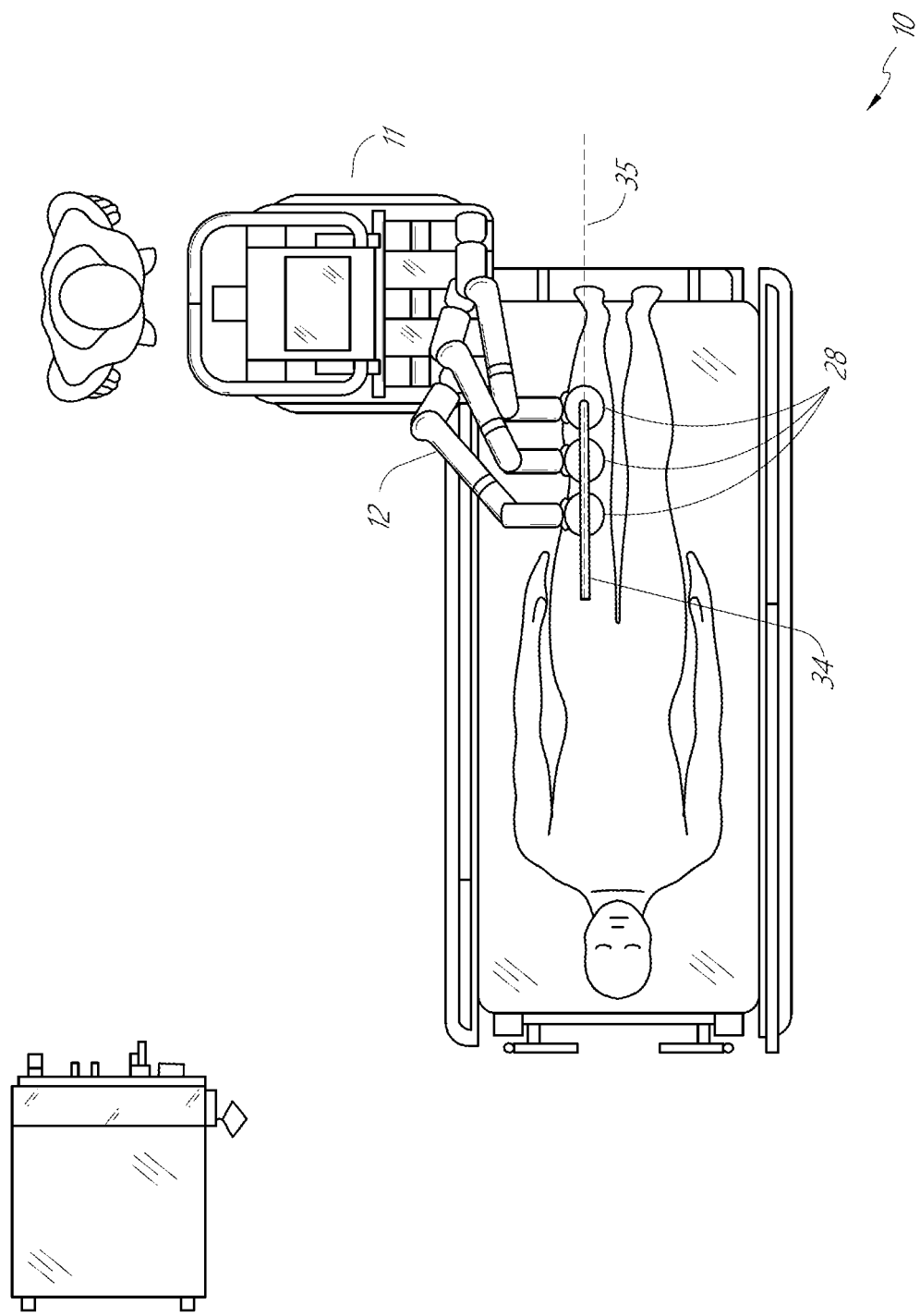
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
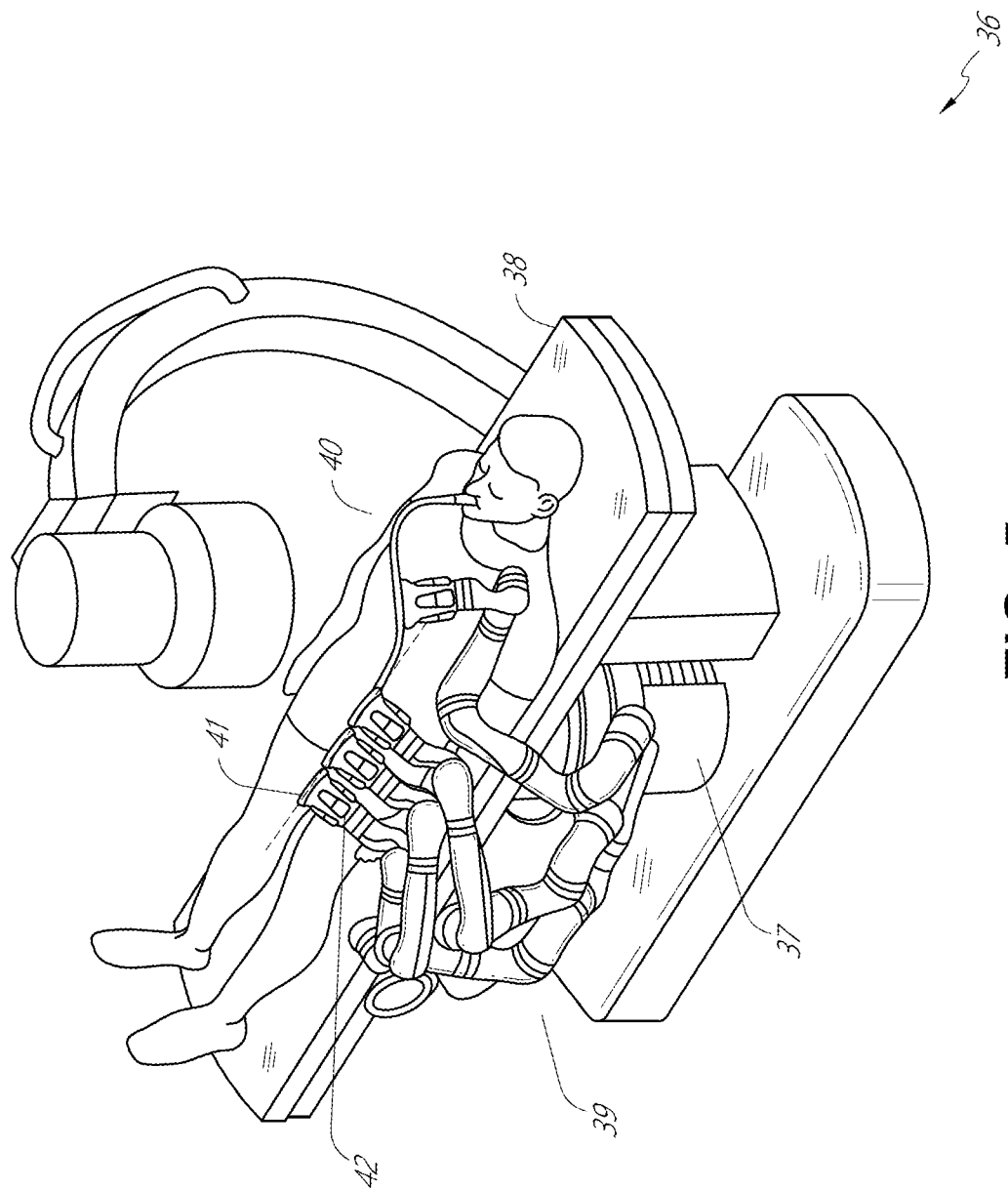
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
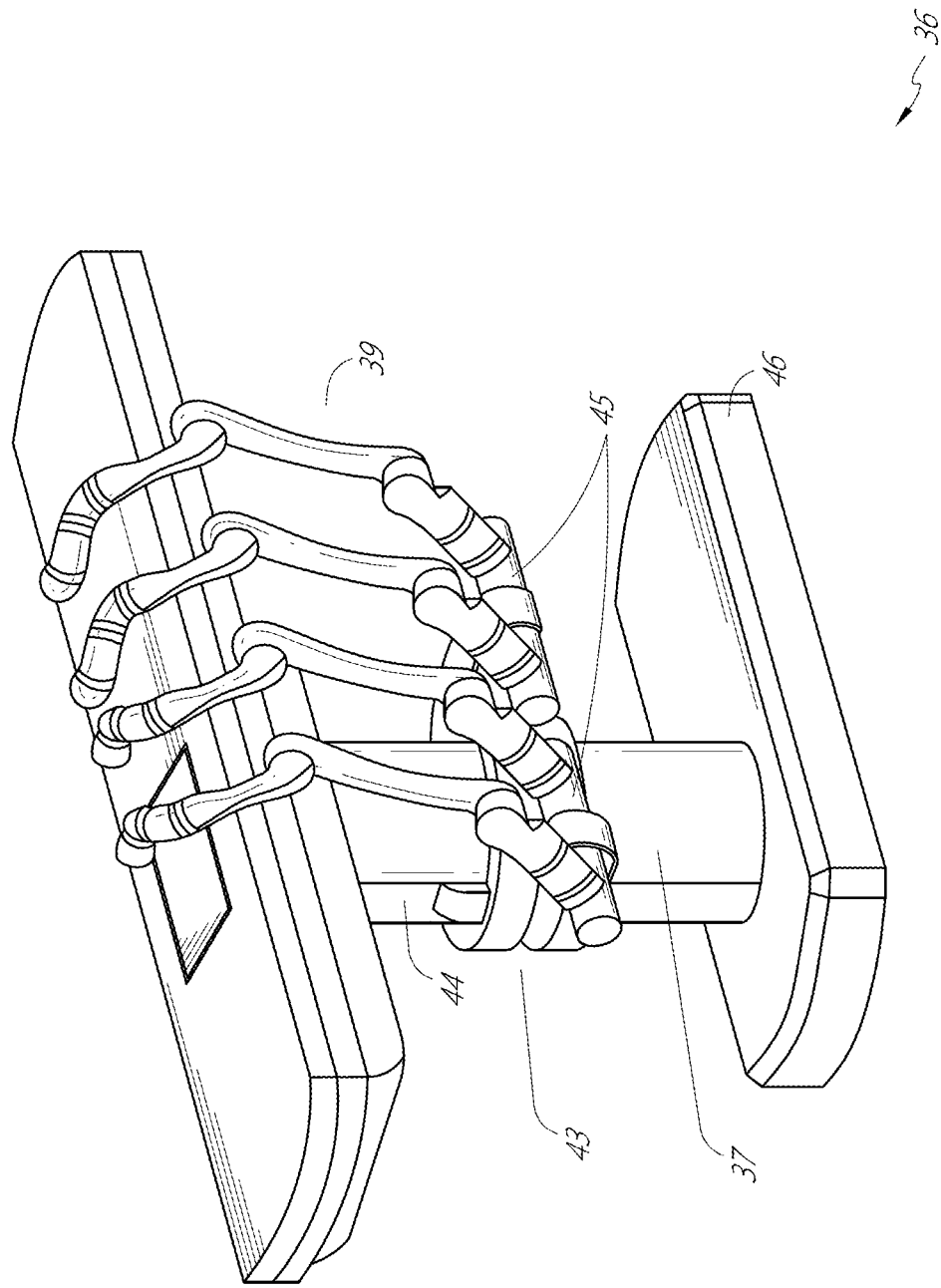
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
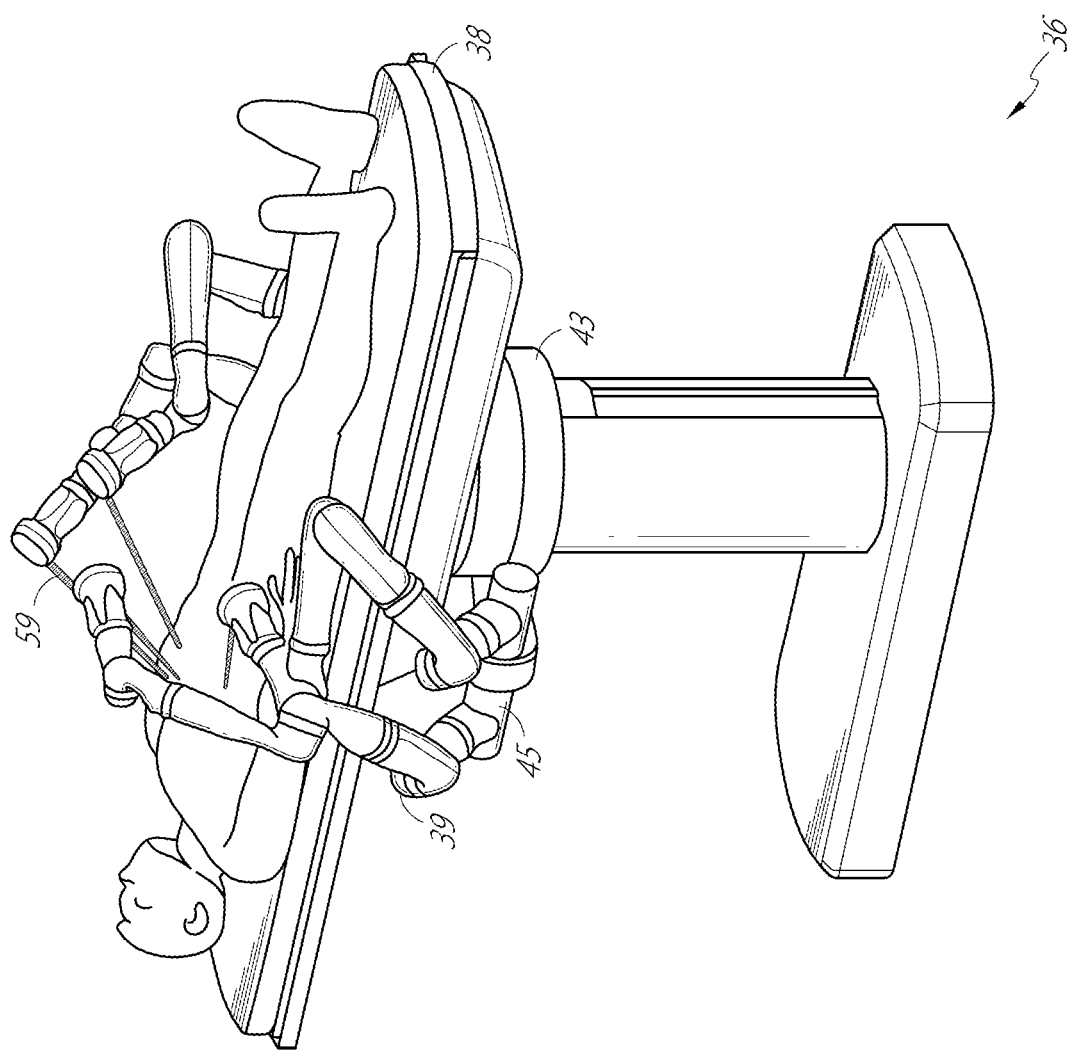
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
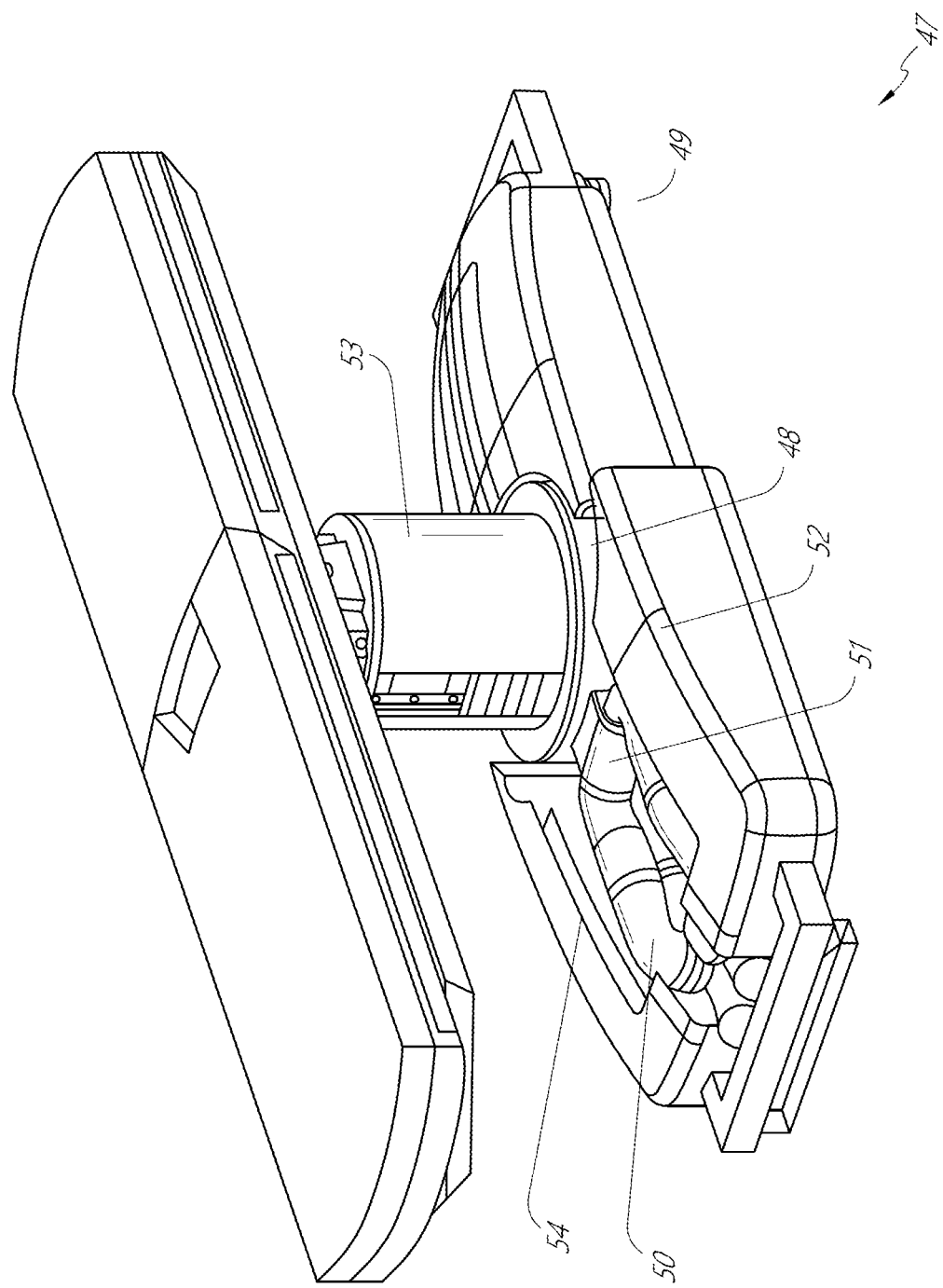
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
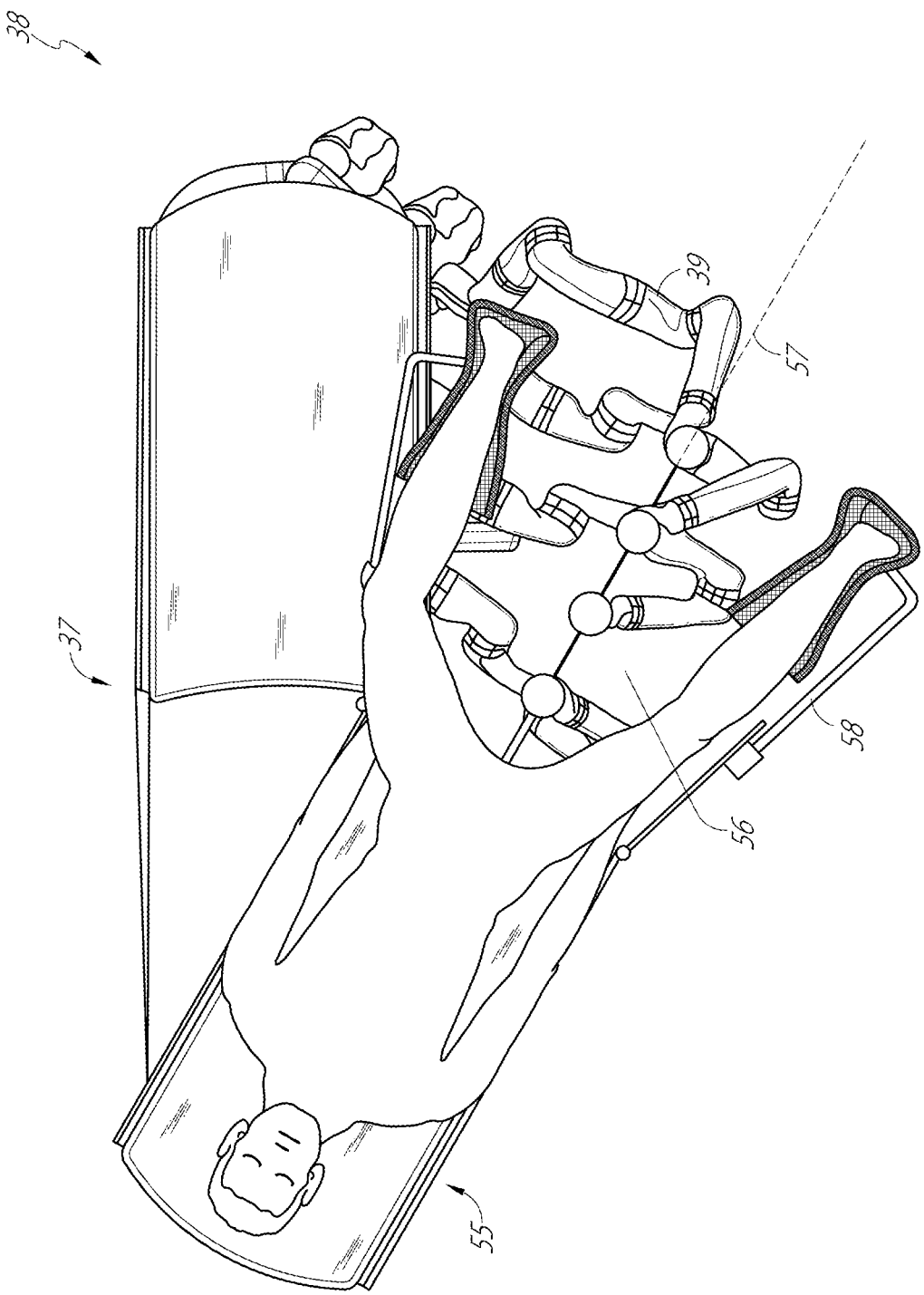
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical or medical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
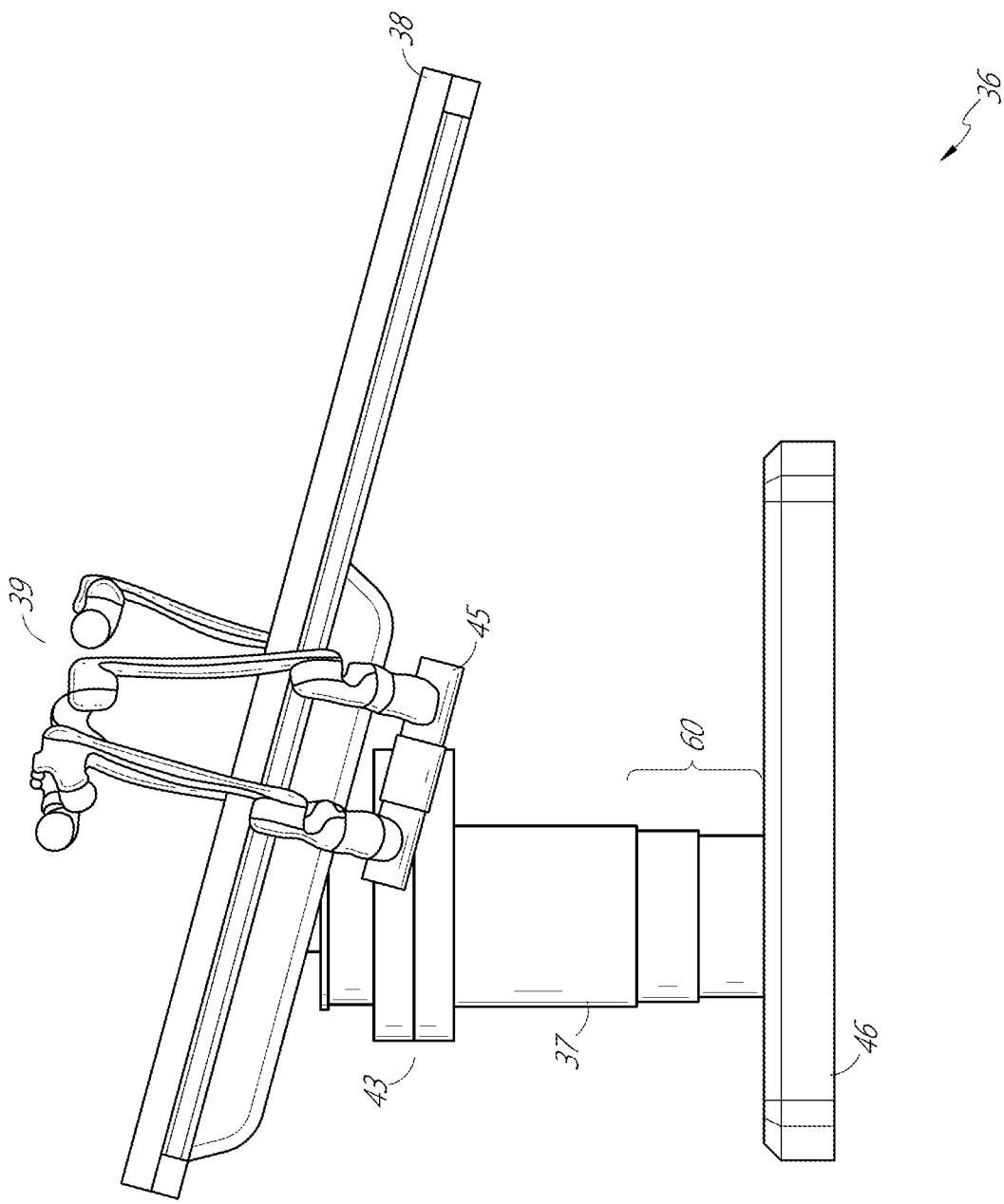
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
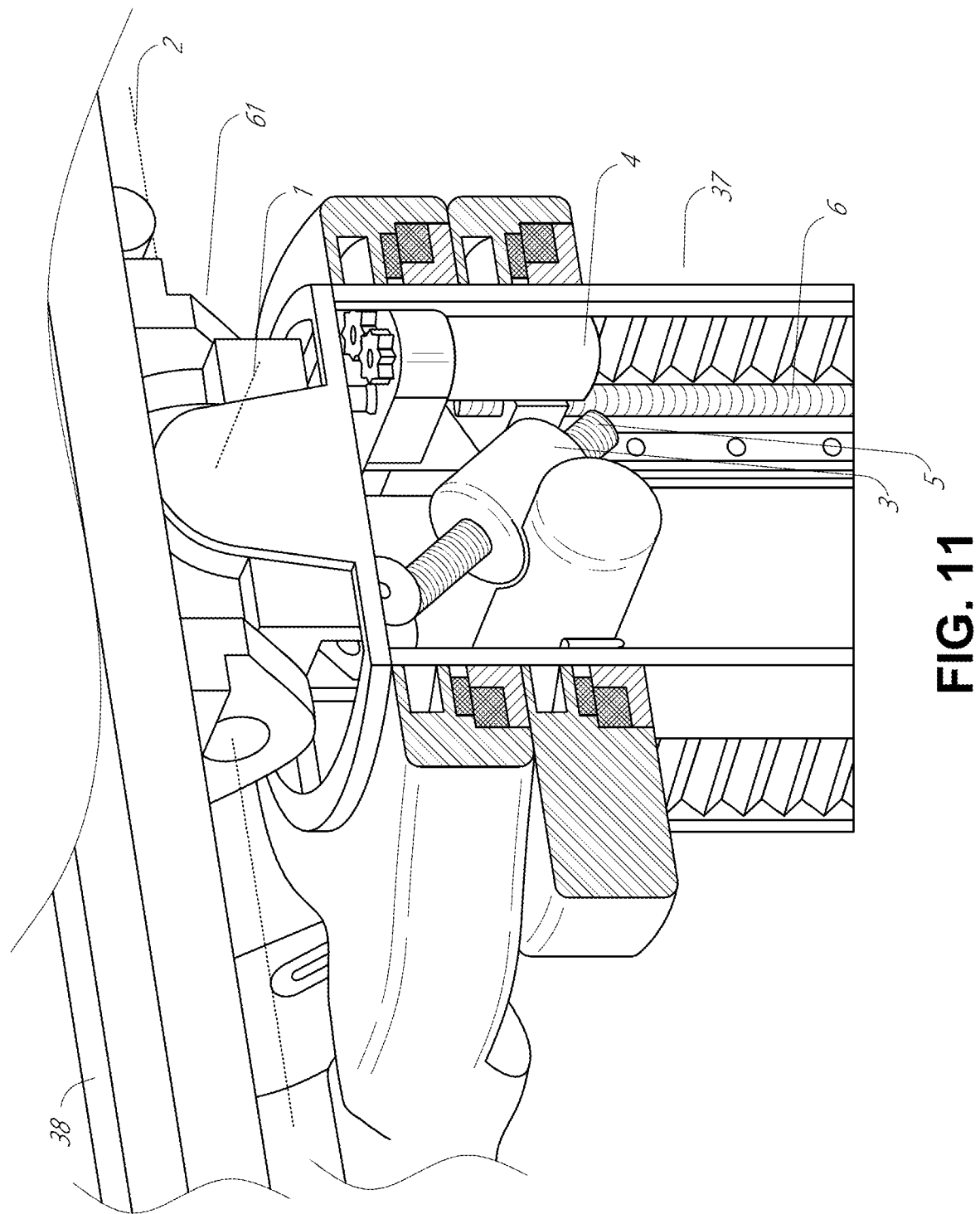
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
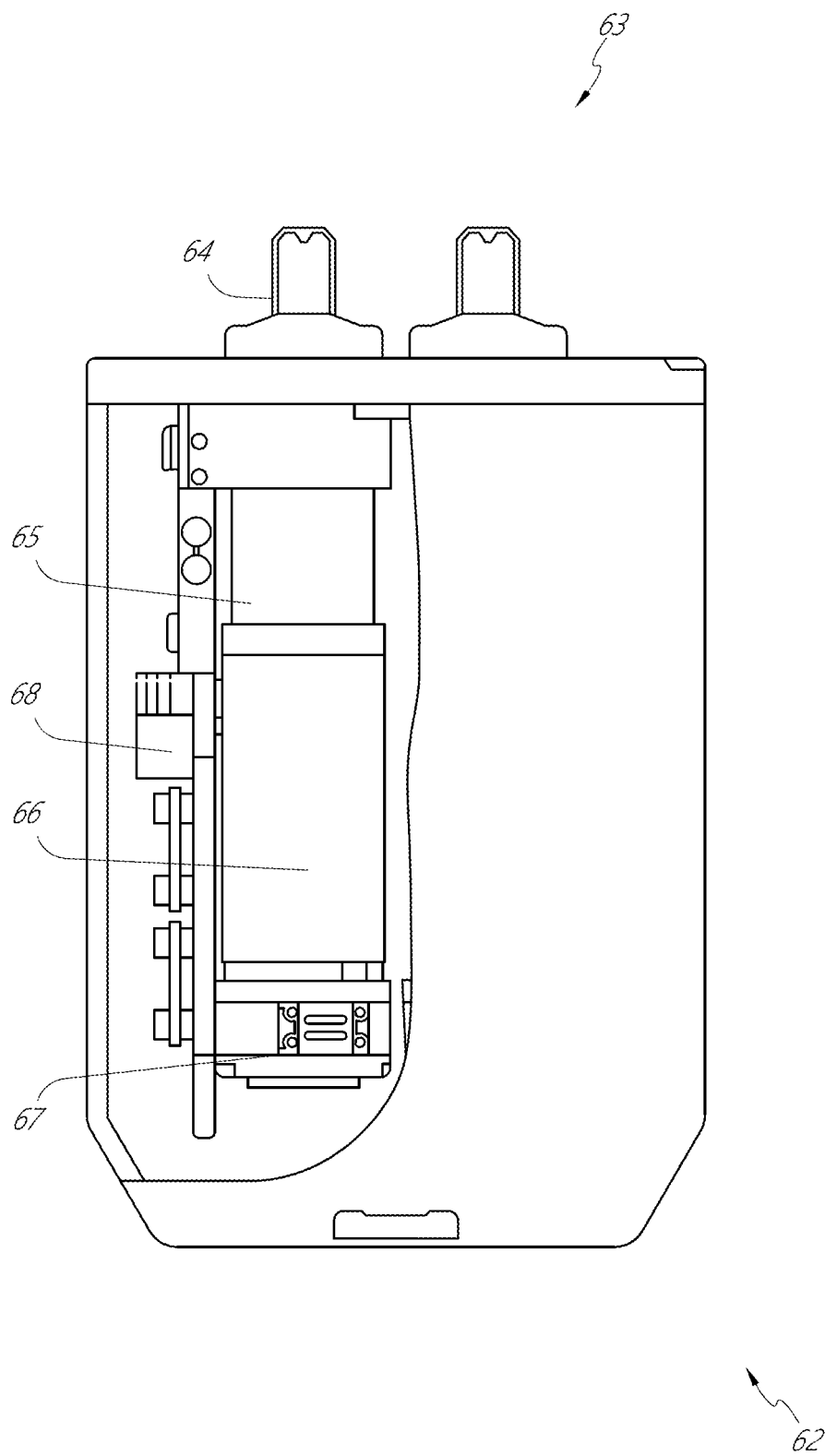
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
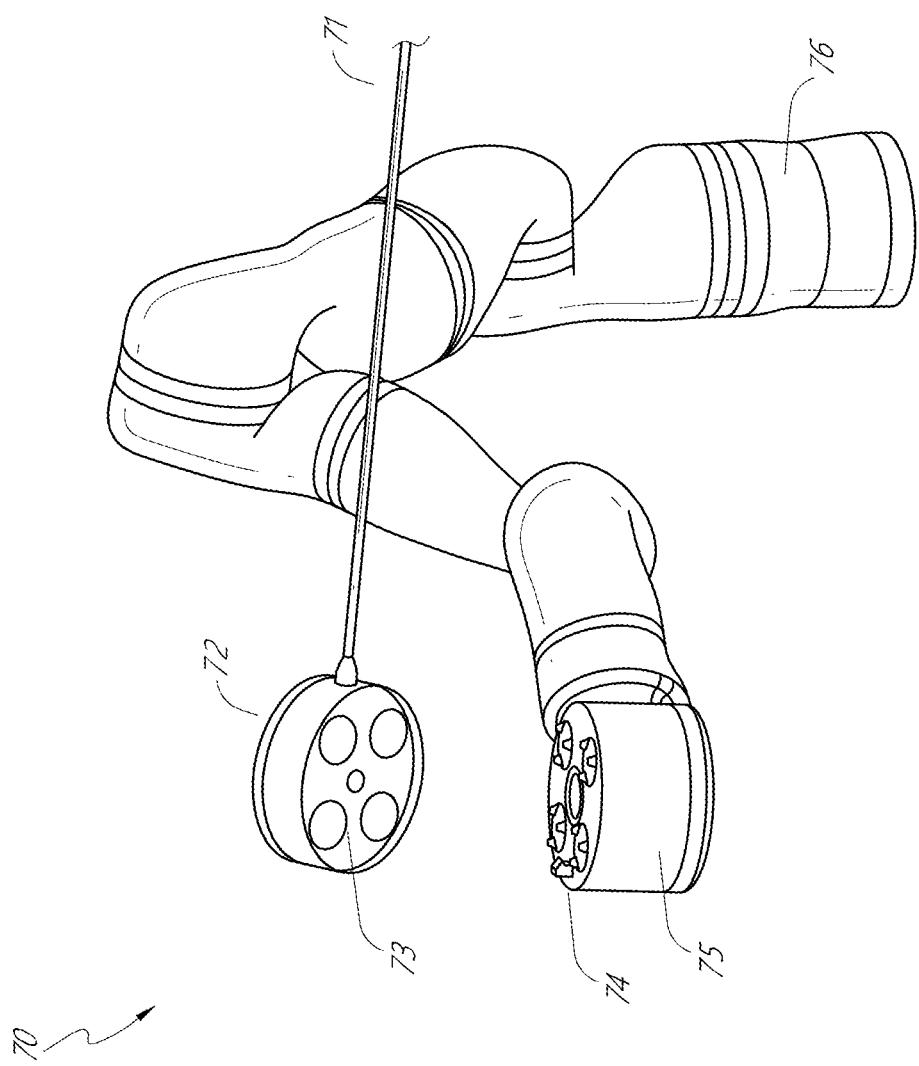
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 14:
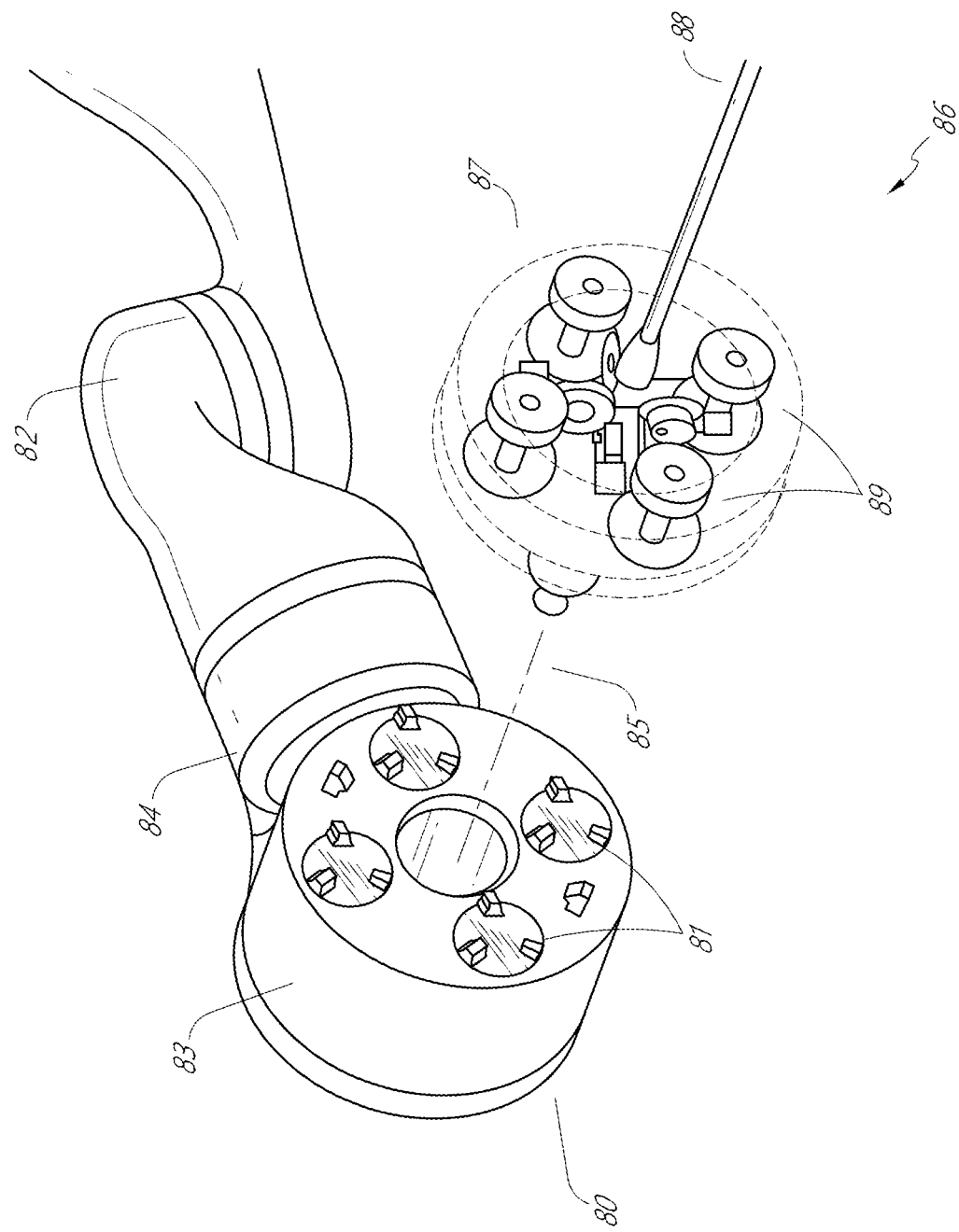
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
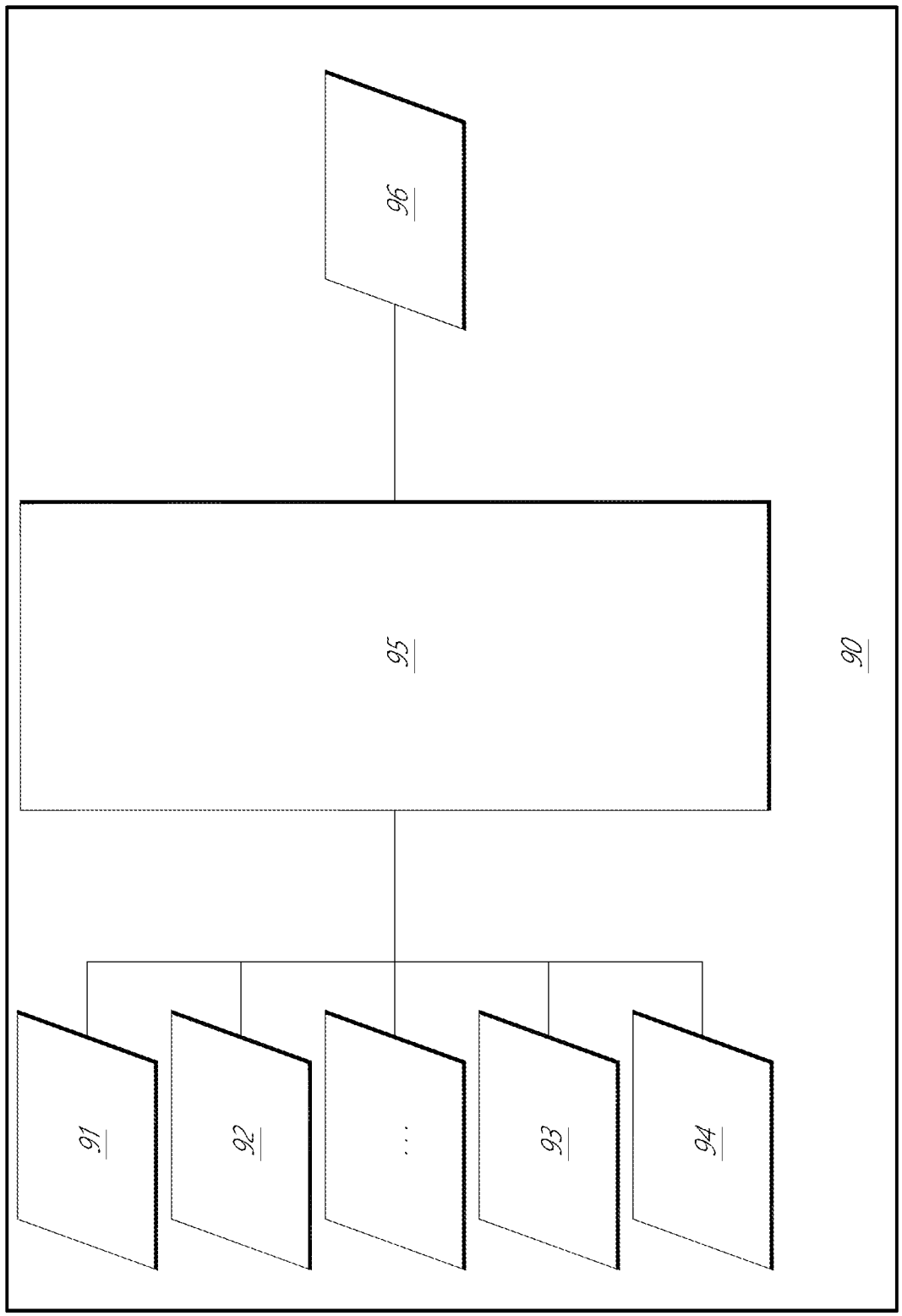
FIG. 15 depicts a block diagram illustrating a localization system that estimates a location of one or more elements of the robotic systems of FIGS. 1-10, such as the location of the instrument of FIGS. 13 and 14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 9194 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 9194 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 9194 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Medical Instruments with Variable Bending Stiffness Profiles

This section relates to medical instruments with variable bending stiffness profiles (also referred to in this application as "variable bending stiffness medical instruments" or in some instances simply as "medical instruments"). In some embodiments, the medical instruments with variable bending stiffness profiles can be used with the robotically-enabled medical systems described above with reference to FIGS. 1-15. For example, in some embodiments, any of the medical instruments described above (e.g., endoscope 13, ureteroscope 32, medical instrument 34, bronchoscope 40, ureteroscope 56, medical instrument 70, and others) can include a variable bending stiffness profile as described herein. In addition to robotic implementations, the medical instruments with variable bending stiffness profiles can also be configured for manual use (i.e., non-robotic use).

The medical instruments with variable bending stiffness profiles can be useful for navigating through tortuous paths within a patient's anatomy. In some embodiments, the medical instruments with variable bending stiffness profiles can be particularly useful in navigating through the pulmonary airways of a patient. The pulmonary airways can be tortuous paths. During some medical procedures the medical instruments can be navigated through the pulmonary airways to detect, diagnose, and/or treat an abnormal growth, such as a tumor. Scopes that are sent into the pulmonary airways often want to travel down incorrect pathways and may struggle to enter into the correct pathways. The medical instruments described herein can be advantageously capable of navigating through the correct pathways due to their variable bending stiffness profiles.

Figure 22:
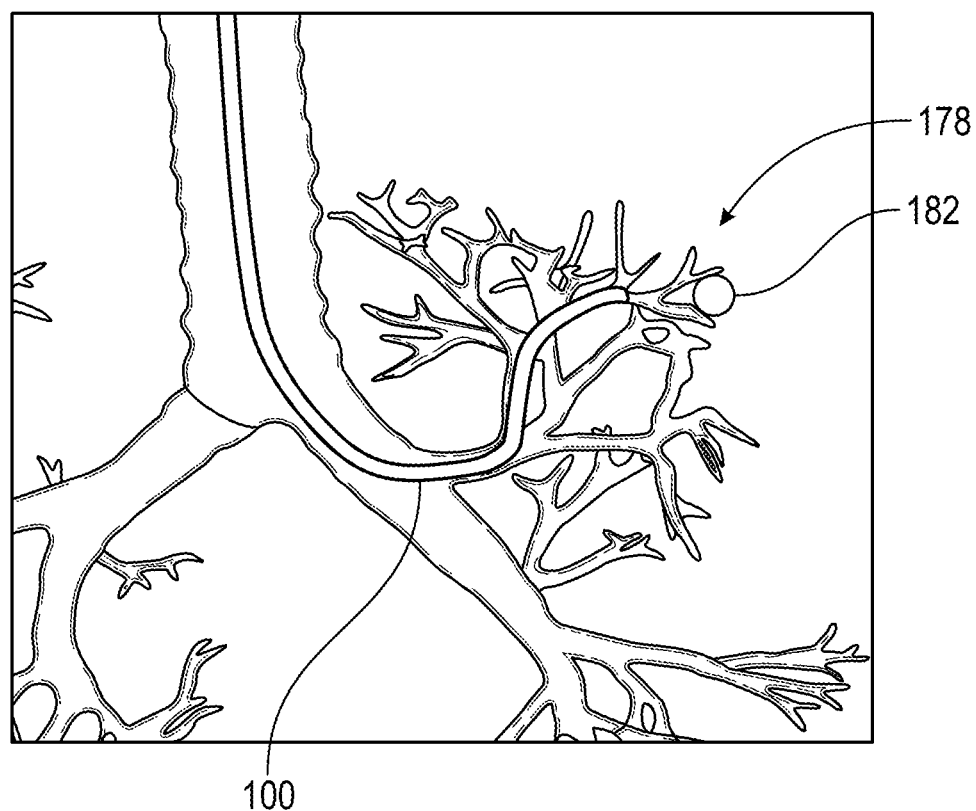
FIG. 22 illustrates an example of a medical instrument navigating within airways of a patient's lung according to one embodiment. The medical instrument can include a variable bending stiffness profile.

FIG. 22 illustrates an example of a medical instrument 100 navigating within a patient's lung. The instrument can be, for example, a scope, a sheath, or a compound instrument comprising a scope positioned within an inner channel of the sheath. In the illustrated example, the instrument 100 is navigated through airways in the lung toward a target site 182 in an upper lobe 178 of the lung. As shown, the airways comprise tortuous paths. As the instrument 100 is inserted into the lung, a distal end of the instrument may be articulated to guide the instrument into particular pathways. However, such navigation can be difficult due to the tortuosity of the lung.

The present application describes medical instruments with variable bending stiffness that are capable of extending through tortuous paths in a patient, including but not limited to the pulmonary airways. In some embodiments, a medical instrument with variable bending stiffness can comprises an elongated shaft. In other embodiments, a medical instrument with variable bending stiffness can be an elongated shaft positioned within an inner channel of a catheter or sheath. The elongated shaft can comprise a leader or scope.

In some embodiments, a variable bending stiffness medical instrument can include an elongated shaft configured for insertion into a patient during a medical procedure that includes a plurality of sections having different bending stiffness properties. As an initial example, a variable bending stiffness medical instrument can include a distal section that has a lower bending stiffness (e.g., that flexes or bends more easily and/or requires less force to flex or bend) than a bending stiffness of a proximal section. In this example, the distal section is more easily bendable so as to facilitate steering or navigation of the medical instrument, while the proximal section is stiff to facilitate pushing the medical instrument through a patient lumen.

Continuing this example, the distal section may include a bending stiffness zone having a substantially constant bending stiffness along its length. The proximal section may also include a bending stiffness zone having a substantially constant bending stiffness along its length. The substantially constant bending stiffness of the distal section can be lower than the bending stiffness of the proximal section (although, in some embodiments, the reverse may also be true).

The variable bending stiffness medical instrument of this initial example can also include a transition zone between the bending stiffness zone of the distal section and the bending stiffness zone of the proximal section. The transition zone may comprise a length over which the bending stiffness gradually varies, for example, from the substantially constant bending stiffness of the bending stiffness zone of the distal section to the substantially constant bending stiffness of the bending stiffness zone of proximal section. In some embodiments, the bending stiffness of the transition section varies at a generally linear slope, rate, or gradient, although this need not be the case in all embodiments. In some embodiments, the slope of the transition zone is substantially constant.

Thus, as shown by the initial example, a variable bending stiffness instrument can include a plurality of bending stiffness zones, each having a bending stiffness that is substantially constant along a length of the bending stiffness zone, and one or more transition zones, each positioned between an adjacent pair of bending stiffness zones in which the bending stiffness gradually transitions between the pair of bending stiffness zones.

Plotting the bending stiffness along the length of the elongated shaft of the variable bending stiffness medical instrument produces a bending stiffness profile. Graphically, each bending stiffness zone (having a substantially constant bending stiffness along its length) is shown as a plateau within the bending stiffness profile, and each transition zone is shown as a slope or ramp (either generally increasing or generally decreasing) between adjacent plateaus. See, for example, FIG. 16B, described in detail below.

The materials and methods of construction (often referred to herein as modalities or properties) of the elongated shaft of a medical instrument determine the bending stiffness at each point along its length. For example, manufacturing the elongated shaft from a stiffer material will produce a higher bending stiffness.

In some embodiments, to produce a medical instrument with a variable bending stiffness, the materials and/or methods of construction can be varied along the length of the elongated shaft. For example, in the embodiment described above, a stiffer material can be used in the proximal section and a more flexible material can be used in the distal section. However, merely varying a single modality (e.g., material or method of construction) along the length may not produce a bending profile having bending stiffness zones and transitions zones as described above. For example, if the only variation in the elongated shaft is the material change described above (a stiff proximal section and a more flexible distal section) the bending stiffness profile would likely comprise only two plateaus connected by a vertical jump. It may not comprise a transition zone having a length over which the bending stiffness gradually transitions. This may disadvantageously create a stress riser or failure point at the transition between the materials.

Thus, as described more fully below, a variable bending stiffness medical instrument may include a construction that varies, in a staggered manner, in more than one modality of the elongated shaft in each transition zone. This may distribute stresses associated with modality changes along a length of the elongated shaft and produce a more gradual (e.g., sloped or ramped) transition zone as described above.

Figure 19A:
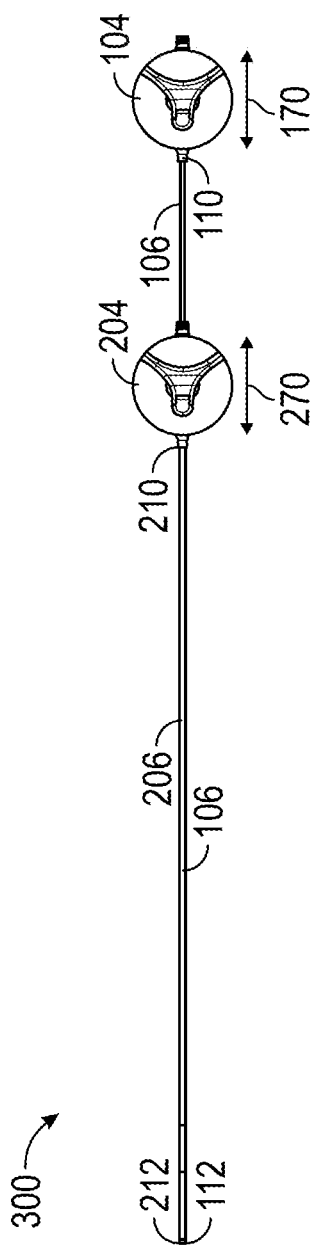
FIG. 19A illustrates a top view of an embodiment of a compound structure, including a scope and a sheath, with the distal end of the scope aligned with the distal end of the sheath.

In some embodiments, a medical instrument with a variable bending stiffness can be configured as a scope (also referred to as a leader), such as an endoscope. The scope can be configured to be inserted through a working or inner channel of a sheath, for example, as shown in FIGS. 19A and 19C. That is, the scope can telescope within the inner channel of the sheath. In some embodiments, the sheath can also be configured as a medical instrument with a variable bending stiffness. Together, the scope and sheath can form a compound structure. In some embodiments, the compound structure has a bending stiffness profile that is different from the bending stiffness profile of either the scope or sheath alone. With the scope positioned within the inner channel of the sheath, the compound structure may comprise a bending profile that is a combination of the individual bending profiles of the scope and the sheath. One skilled in the art will appreciate that the term "compound structure" encompasses all parts of the scope and the sheath whenever the scope is positioned within the inner channel of the sheath, including parts of the scope that may extend distally from the sheath, or parts of the sheath that may extend distally from the scope.

Further, as will be described more fully below, it is possible to modulate (i.e., change or vary) the bending stiffness profile of the compound structure by moving the scope relative to the sheath, or vice versa. For example, both the scope and the sheath can include a plurality of different bending stiffness zones separated by transition zones. When, for example, the distal tip of the scope is aligned with the distal tip of the sheath, the plurality of different bending stiffness zones and transition zones line up in a first way to produce a first combined bending stiffness profile for the compound structure. When, for example, the scope is further inserted through the sheath such that the distal tip of the scope extends beyond the distal tip of the sheath, the plurality of different bending stiffness zones and transition zones line up in a second way to produce a second combined bending stiffness profile that may be different than the first combined bending stiffness profile.

In some embodiments, the first combined bending stiffness profile may include a first number of bending stiffness zones and the second combined bending stiffness profile may include a second number of bending stiffness zones. Thus, it is possible to vary the number of bending stiffness zones of the compound structure by moving the scope relative to the sheath or vice versa. Although two bending stiffness profiles for the compound structure are mentioned in this example, it will be appreciated that there are many ways in which the scope can be positioned relative to the sheath (e.g., by varying the relative distance between the distal end of the scope and the distal end of the sheath) and each of these can produce a unique bending stiffness profile for the compound structure.

In some embodiments, a compound structure may comprise a bending stiffness profile wherein the bending stiffness of the compound structure varies depending on the position of the sheath relative to the scope. As the bending stiffness varies, the bending stiffness may assume a range or area of coverage along the length of the scope. Different regions of bending stiffness are shown below, such as for example in FIG. 16D.

In some embodiments that include a compound structure having a scope positioned within an inner channel of a sheath, the scope and the sheath may comprise different lengths. For example, the scope and the sheath might not be coextensive in length. In some embodiments, the sheath is shorter than the scope.

The ability to modulate or change the bending stiffness profile of the compound structure (e.g., the combined scope and sheath) can be advantageous for various reasons. For example, during a procedure, a physician (or in some instances, a robotically-enabled medical system) can adjust the bending stiffness profile of the compound structure in order to facilitate navigation of a particular portion of a patient's anatomy. This can be accomplished by, for example, moving the scope relative to the sheath.

As a more particular example, during bronchoscopy, a physician may examine airways in a patient's lungs, such as bronchi and bronchioles. For example, as shown in FIG. 22, during the procedure, a medical instrument 100 (e.g., a scope and sheath) may be inserted into the patient's mouth and passed down the patient's trachea into his or her lung airways towards a tissue site identified for subsequent diagnosis and/or treatment (e.g., target 182). The pulmonary airways are tortuous paths that can be particularly difficult to navigate. It can be particularly challenging to navigate the secondary bronchi, tertiary bronchi, bronchioles, and the upper lobes 178 of the lung. Often, navigating in these portions of the lung requires the medical instrument to make tight turns. The physician may find that a particular bending stiffness profile of the instrument is not well suited for a particular turn or maneuver. For example, with the particular bending stiffness profile the medical instrument may be inclined to travel down an incorrect pathway and/or may struggle to enter a correct pathway. In such a situation, the physician can modulate or change the bending stiffness profile of the medical instrument by moving the scope relative to the sheath (e.g., inserting the scope further through the sheath such that the scope extends from the sheath, positioning the scope and sheath such that their distal ends are aligned, or retracting the scope within the sheath such that the scope extends beyond the sheath) to modulate the bending stiffness profile. The physician can position the scope and the sheath such that the medical instrument has a bending stiffness profile better suited for the desired maneuver and then perform the maneuver.

These and other features and advantages of medical instruments with variable bending stiffnesses will now be described in greater detail with reference to several embodiments illustrated in the figures. The illustrated embodiments are provided by way of example and are not intended to be limiting.

A. Example Medical Instruments with Variable Bending Stiffness Profiles.

Figure 16A:
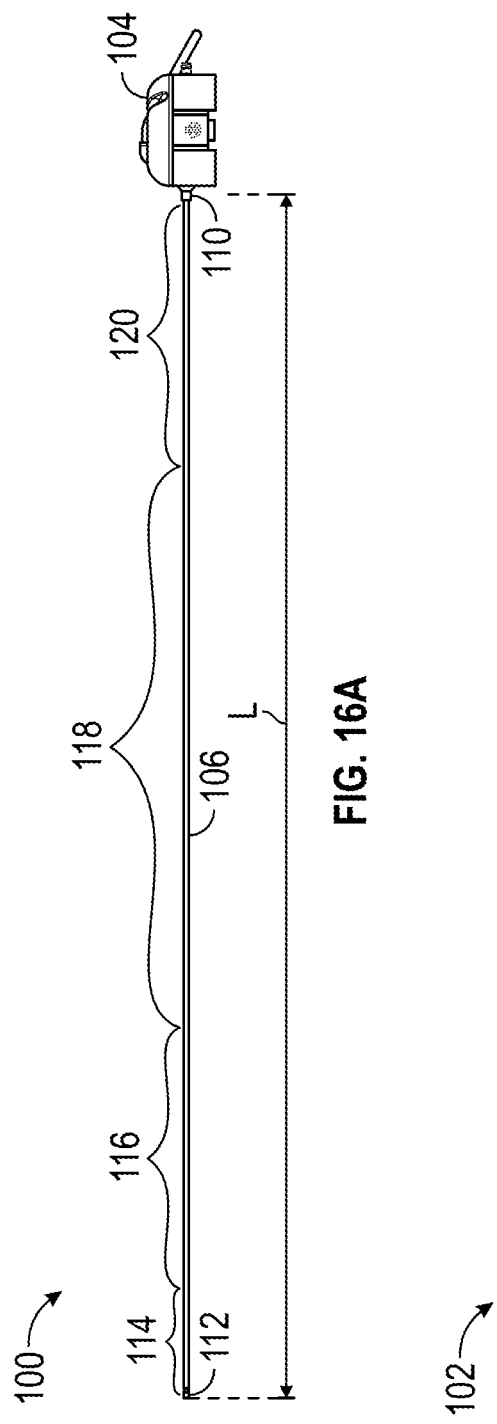
FIG. 16A is a side view of an embodiment of a medical instrument configured as an endoscope and having a variable bending stiffness profile.
Figure 16B:
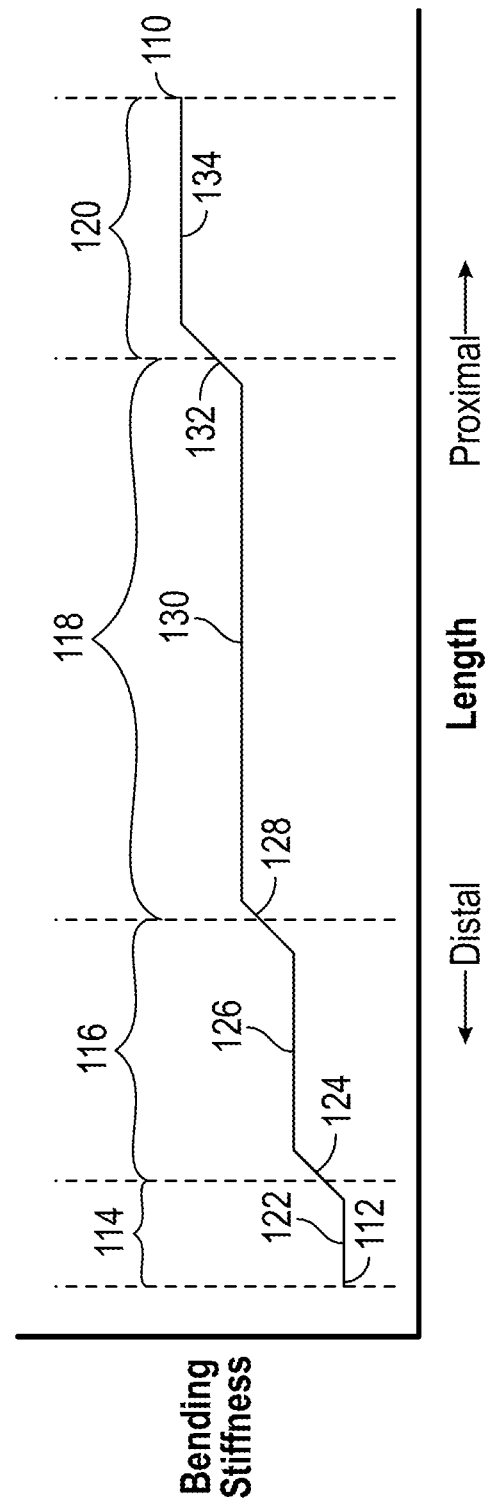
FIG. 16B illustrates an example variable bending stiffness profile of the medical instrument of FIG. 16A.
Figure 16C:
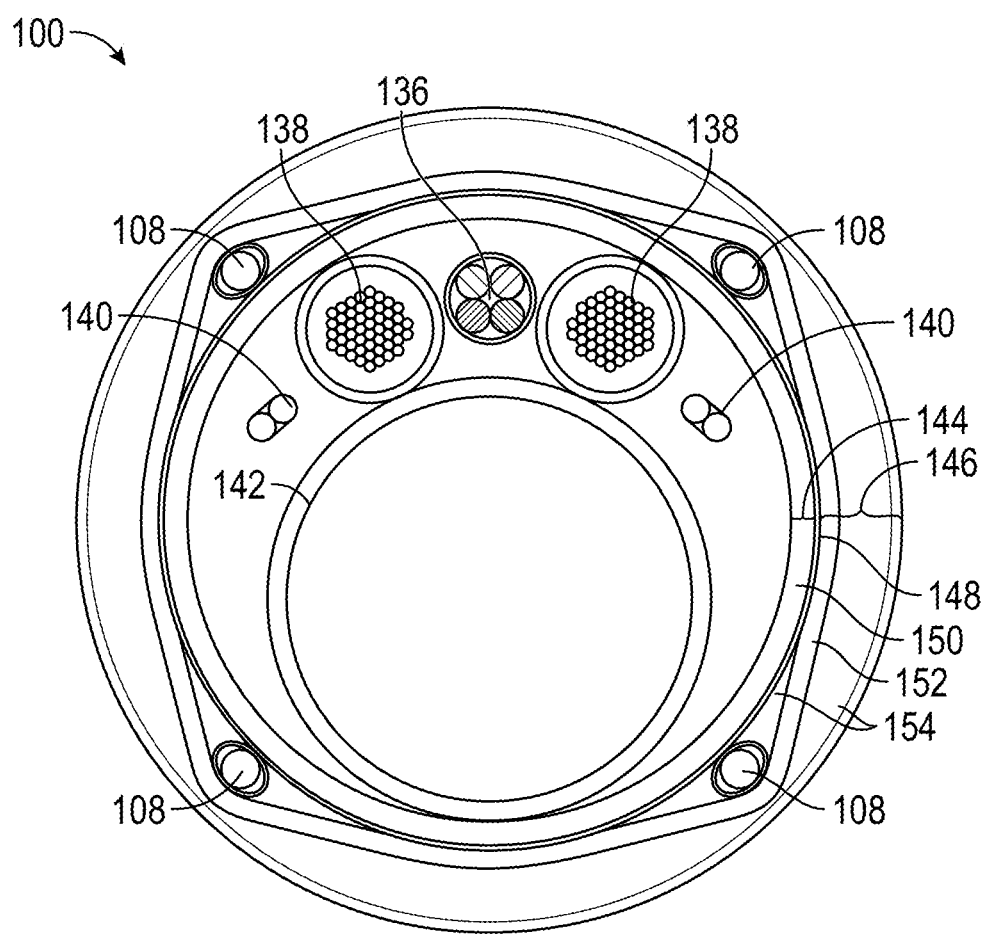
FIG. 16C illustrates a cross-sectional view of the medical instrument of FIG. 16A, showing an example multi-modality construction thereof.

FIGS. 16A-16D relate to an embodiment of a medical instrument 100 having an example variable bending stiffness profile 102. In the illustrated embodiment, the medical instrument 100 is configured as a catheter, such as a scope (e.g., an endoscope or bronchoscope). The principles and features described with reference to this illustrated example, however, may be applicable to other types of medical instruments as well, for example, other types of scopes (e.g., ureteroscopes, bronchoscopes, etc.), sheaths, etc. FIG. 16A is a side view of the medical instrument 100. FIG. 16B illustrates an example variable bending stiffness profile 102 of the medical instrument 100. FIG. 16C illustrates a cross-sectional view of the medical instrument 100 showing an example multi-modality construction thereof. FIG. 16D schematically illustrates an example of how the individual modalities of the multi-modality construction can be varied to achieve the variable bending stiffness profile 102 of the medical instrument 100.

As illustrated in FIG. 16A, the medical instrument 100 includes an instrument base 104 and an elongated shaft 106. The instrument base 104, which can also be referred to as a handle, can be configured to attach to an instrument drive mechanism, for example, as shown in FIG. 13 (showing an example instrument base 72 configured to attach to an instrument drive mechanism 75). The instrument drive mechanism may electronically and/or mechanically couple to the instrument base 104 such that the medical instrument 100 can be robotically controlled. Although the illustrated embodiment is configured for robotic control, in some embodiments, the instrument base 104 may be replaced with an instrument handle configured to enable manual operation and control of the medical instrument 100.

The elongated shaft 106 can be configured for insertion into a patient during a medical procedure. For example, the elongated shaft 106 can be designed to be delivered through either an anatomical opening or lumen, for example, as in endoscopy, or a minimally invasive incision, for example, as in laparoscopy. In the case of bronchoscopy, the elongated shaft 106 can be inserted through an introducer and into a patient's mouth, down the trachea, and into the lung. To navigate within the patient's body, at least a portion of the elongated shaft 106 may be flexible. In some embodiments, the elongated shaft 106 can include one or more pull wires 108 (for example, as shown in FIG. 16C). The one or more pull wires 108 can be actuable to bend one or more portions of the elongated shaft 106 in order to control the shape or pose thereof. For example, during a procedure, the one or more pull wires 108 can be actuated to guide the elongated shaft 106 through the patient's anatomy to a target site. In the case of bronchoscopy, this can involve guiding the elongated shaft through a complex network of branching airways. In some embodiments, the elongated shaft 106 can comprise one or more sensors to assist in localization and/or navigation of the elongated shaft 106 in a patient (for example, as described above with reference to FIG. 15). In addition or alternatively, in some embodiments, the elongated shaft 106 can include one or more optical fibers for determining a shape of the elongated shaft 106.

The elongated shaft 106 can extend between a proximal end 110 and a distal end 112. The proximal end 110 can extend from and be attached to the instrument base 104. The distal end 112 can be the leading end of the elongated shaft 106 of the medical instrument 100. For example, the distal end 112 can be the first point introduced into the patient, and, during a medical procedure, the medical instrument 100 can be guided or driven such that the distal end 112 is advanced toward a target site within the patient. In some embodiments, the distal end 112 includes various features for visualizing and/or treating the target site. For example, the distal end 112 can include a camera, a light source, an end effector (e.g., graspers, cutters, basketing device, etc.), and/or an opening to a working channel through which additional medical tools or instruments can be advanced. Medical tools or instruments that can be delivered through the working channel include, but are not limited to, guidewires, diagnostic and biopsy tools (e.g., ultrasound devices, wires, brushes and other dithering and non-dithering tools), and tools for delivering therapeutic effects (e.g., tools for brachytherapy). While in some embodiments, the camera can be delivered down a channel that is different from other tools or instruments, in other embodiments, the camera can be delivered through the same working channel as other medical tools or instruments. For example, in some embodiments, the camera can be delivered through a working channel in the scope and subsequently removed to make room for a diagnostic and/or treatment tools (such as a dithering or non-dithering tool) to detect and/or treat an abnormal growth. Certain features are illustrated in FIG. 16C, described in greater detail below.

The elongated shaft 106 includes a length L measured between the proximal end 110 and the distal end 112. The length L may be selected so as to facilitate a medical procedure or a range of medical procedures for which the medical instrument 100 will be used. Relevant factors for selecting the length L may include path length to the target site, patient anatomy, patient size, drivability and control, operating environment conditions (e.g., placement or robotic arms within an operating room), etc. In some embodiments, for example, the length L may be between about 700 and 1200 mm, between about 800 and 1100 mm, or between about 900 and 1000 mm. In one example, the length L is about 930 mm.

In the illustrated embodiment, the elongated shaft 106 includes four different sections: a bending section (also referred to an active bending section) 114, a passive bending section 116, an internal shaft section 118 (also referred to as a tracking section), and an external shaft section 120. The sections can be arranged serially along the length L of the elongated shaft 106 between the distal end 112 and the proximal end 110. Although four sections are illustrated, in some embodiments, a medical instrument can include more of less sections. For example, a medical instrument can include one, two, three, four, five, six, seven, or more sections.

Each section can be configured to provide a different flexibility or bending stiffness to facilitate the medical procedure and/or improve the drivability and control of the medical instrument 100. For example, in some embodiments, more distally located sections (e.g., active bending section 114 and passive bending section 116) are more flexible to facilitate maneuverability of the elongated shaft 106, and more proximally located sections (e.g., internal shaft section 118 and external shaft section 120) are stiffer to provide pushability for the elongated shaft 106, while preventing or reducing the likelihood of buckling. Further, in some embodiments, the active bending section 114 can be more flexible than the passive bending section 116, and the external shaft section 120 can be stiffer than the internal shaft section 118. Other arrangements are also possible.

In some embodiments, the active bending section 114 provides steerability to the distal end of the medical instrument 100. In some embodiments, the passive bending section 116 provides enough flexibility to advantageously track up into the peripheral or upper lobes of the lung, for example, in the case of the bronchoscopy. In some embodiments, the internal shaft section 118 is flexible enough to be inserted through an introducer and tube bends, but pushable/rigid enough to provide support for the elongated shaft 106. In some embodiments, the external shaft section 120 is a part of the elongated shaft 106 that remains external to the patient during a procedure (e.g., does not enter the introducer) and is stiff enough to provide support for the distal end 112 of the elongated shaft 106 and prevent buckling.

In some embodiments, the active bending section 114 can be between about 50 and 80 mm, or approximately 65 mm. In some embodiments, the active bending section 114 defines the articulation radius of the scope. In some embodiments, the passive bending section 116 can be between about 150 mm and 190 mm, or approximately 170 mm. In some embodiments, the internal shaft section 118 can be between about 540 mm and 600 mm, or approximately 572 mm. In some embodiments, the external shaft section 120 can be between about 90 mm and 150 mm, or approximately 123 mm. Advantageously, the different lengths of the four different zones are designed to desirably align the elongated shaft 106 with portions of an overlying sheath, thereby creating a compound structure with desired variable stiffnesses along different lengths as described below. In some embodiments, other lengths for one, more, or all of these sections are also possible.

In some embodiments, to achieve these different functions, each section comprises different bending stiffness characteristics or properties. The preceding paragraphs have described the sections in terms of flexibility and stiffness. It will be appreciated that each of these properties is related to bending stiffness. For example, bending stiffness is generally inversely related to flexibility: as bending stiffness increases, flexibility decreases. Bending stiffness is also generally proportionally related to stiffness: as bending stiffness increases, stiffness increases.

FIG. 16B illustrates a representative bending stiffness profile 102 of the elongated shaft 106 of the medical instrument 100. The bending stiffness profile 102 illustrates the bending stiffness of the elongated shaft 106 as a function of or along its length L between the distal end 112 and the proximal end 110. In the illustrated example, the x-axis represents the length L of the elongated shaft 106 between the distal end 112 and the proximal end 110, and the y-axis is a measure of the max-force bending stiffness of the elongated shaft 106 measured in Newtons (N). In some examples, to calculate the max-force bending stiffness, a cantilever bend test is performed. In a cantilever bend test, a force tester (e.g., an anvil) is used to push down (bend) the elongated shaft 106 to a fixed distance. The force required to bend the elongated shaft 106 to the fixed distance is measured as the max-force bending stiffness, although technically, the force that is measured is the reaction force from the elongated shaft 106. In general, the lower the max-force bending stiffness, the more flexible the scope.

As shown by the example bending stiffness profile 102 of FIG. 16B, the bending stiffness of the elongated shaft 106 varies or changes along its length. Accordingly, the medical instrument 100 comprises a variable bending stiffness profile 102.

In the illustrated embodiment and as seen in the example bending stiffness profile 102, the elongated shaft 106 of the medical instrument 100 comprises a plurality of bending stiffness zones wherein the bending stiffness is substantially constant (represented as plateaus within the bending stiffness profile 102) and a plurality of transition zones (represented as ramps within the bending stiffness profile 102). As illustrated, the medical instrument 100 includes four bending stiffness zones of substantially constant bending stiffness and three transition zones, with each transition zone positioned between a pair of adjacent bending stiffness zones. In the illustrated example, the medical instrument 100 includes (arranged distally to proximally) a first bending stiffness zone 122 of substantially constant bending stiffness, a first transition zone 124, a second bending stiffness zone 126 of substantially constant bending stiffness, a second transition zone 128, a third bending stiffness zone 130 of substantially constant bending stiffness, a third transition zone 132, and a fourth bending stiffness zone 134 of substantially constant bending stiffness.

In some embodiments, each section can be viewed as a zone of bending stiffness, such that the elongated shaft 106 includes four zones of bending stiffness, with each zone from the most distal bending section 114 to the most proximal section 120 increasing in stiffness. In some embodiments, the first bending stiffness zone 122 has a bending stiffness between about 1 N to 5 N; the second bending stiffness zone 126 has a bending stiffness between about 5 N to 10 N; the third bending stiffness zone 130 has a bending stiffness between about 15 N to 25 N; and the fourth bending stiffness zone 134 has a bending stiffness greater than 30 N. In some embodiments, one, more, or all of the bending stiffness zones can comprise other bending stiffnesses (e.g., higher or lower) than the listed values.

Although four bending stiffness zones and three transition zones are shown and described, other embodiments may include other numbers of bending stiffness zones and transition zones. For example, a medical instrument could include two, three, four, five, six, or more bending stiffness zones of substantially constant bending stiffness, separated by one, two, three, four, five, or more transition zones.

As used herein, the term "bending stiffness zone having a substantially constant bending stiffness" (sometimes referred to only as a "bending stiffness zone") refers to a length of the elongated shaft 106 over which the bending stiffness remains substantially constant. In some examples, the length may be between approximately 10 mm and 200 mm. In some embodiments, the length is approximately 10 mm, 25 mm, 50 mm, 75 mm, 100 mm, 150 mm, 200 mm, 300 mm, 400 mm, 500 mm or longer. In some examples, "substantially constant" means that, over the length, the bending stiffness varies by less than about 2.5%, 5%, or 10%, the average bending stiffness value of the elongated shaft 106 over the length. In some examples, "substantially constant" means that, over the length, the bending stiffness varies by less than a threshold force value, such as 0.1N, 0.25 N, 0.5 N, 1 N, 5 N, or 10 N.

As used herein, "transition zone" refers to a length of the elongated shaft 106 over which the bending stiffness varies or transitions from one value to another value. In some examples, the length may be between approximately 10 mm and 200 mm. In some embodiments, the length is between 10 mm and 200 mm, or approximately 10 mm, 25 mm, 50 mm, 75 mm, 100 mm, 150 mm, 200 mm, 300 mm, 400 mm, 500 mm or longer. In some embodiments, a transition zone is positioned between a pair of bending stiffness zones of substantially constant bending stiffness, and the transition zone comprises a length over which the bending stiffness transitions from the substantially constant bending stiffness of the bending stiffness zone on one side of the transition zone to the substantially constant bending stiffness of the bending stiffness zone of the bending stiffness zone on the other side of the transition zone.

In some embodiments, within a transition zone, the bending stiffness may vary at a generally or substantially constant or linear rate such that the slope of the transition zone is substantially constant. In this context, in some examples, "substantially constant" means that, over the length of the transition zone, the slope varies by less than about 2.5%, 5%, or 10%, the average slope value of the elongated shaft 106 over the length of the transition zone. In some embodiments, it may be preferred to have transition zones wherein the bending stiffness varies at a generally or substantially constant or linear rate. However, transition zones need not be linear in all embodiments. In some embodiments, the transition zones have a curved ramp shape.

In the illustrated embodiment, the first bending stiffness zone 122 has the lowest substantially constant bending stiffness, the second bending stiffness zone 126 has a substantially constant bending stiffness that is higher than that of the first bending stiffness zone 122, the third bending stiffness zone 130 has a substantially constant bending stiffness that is higher than that of the second bending stiffness zone 126, and the fourth bending stiffness zone 134 has a substantially constant bending stiffness that is higher than that of the third bending stiffness zone 130. Thus, the bending stiffness of the medical instrument 100 can generally increase from the distal end 112 to the proximal end 110. This need not be the case in all embodiments. For example, the bending stiffness could increase, decrease, and then increase again, or generally decrease.

Further, in the illustrated embodiment, the transition zones 124, 128, 132 include generally or substantially constant slopes. It will be appreciated that the slope of each transition zone can vary. For example, the slope of the first transition zone 124 can be less than the slope of the second transition zone 128, and the slope of the second transition zone 128 can be less than the slope of the third transition zone 132. Again, this need not be the case in all embodiments.

For reference, FIG. 16B also illustrates how, in one example, the bending stiffness profile 102 aligns with the active bending section 114, the passive bending section 116, the internal shaft section 118, and the external shaft section 120. In the illustrated embodiment, each section includes one bending stiffness zone of substantially constant bending stiffness. For example, the first bending stiffness zone 122 is positioned in the active bending section 114, the second bending stiffness zone 126 is positioned in the passive bending section 116, the third bending stiffness zone 130 is positioned in the internal shaft section 118, and fourth bending stiffness zone 134 is positioned in the external shaft section 120. The elongated shaft 106 can be configured such that the substantially constant bending stiffness of the bending stiffness zone positioned within the section facilitates or enables the section to perform its specified function.

The transition zones 124, 128, 132 provide lengths over which the bending stiffness of the elongated shaft 106 can gradually vary from a lower value to a higher value (or vice versa). Having regions where the bending stiffness varies gradually (as opposed to abruptly) can help to avoid stress risers and failure points within the elongated shaft 106.

In some embodiments, each section includes at least one bending stiffness zone of substantially constant bending stiffness. In some embodiments, each section includes exactly one bending stiffness zone of substantially constant bending stiffness. In some embodiments, one or more sections include more than one bending stiffness zone of substantially constant bending stiffness.

In the illustrated embodiment, the transition zones 124, 128, 132 are positioned to overlap adjacent sections. For example, the first transition zone 124 is positioned between and partially overlaps the active bending section 114 and the passive bending section 116. The second transition zone 128 is positioned between and partially overlaps the passive bending section 116 and the internal shaft section 118. And the third transition zone 132 is positioned between and partially overlaps the internal shaft section 118 and the external shaft section 120. Other arrangements and positions for the transition zones are also possible. For example, a transition zone could be positioned entirely within one section, for example, at a distal end of the section, at a proximal end of the section, or along the length of a section between the proximal and distal ends.

As mentioned above, the materials and methods of construction (referred to herein as modalities or properties) of the elongated shaft 106 of a medical instrument 100 determine the bending stiffness, and to produce a medical instrument 100 with a variable bending stiffness (e.g., with a bending stiffness profile as illustrated in FIG. 16), the materials and/or methods of construction can be varied along the length of the elongated shaft 106. Further, to achieve the gradual transition zones described above, the elongated shaft 106 can be manufactured with a plurality of modalities and that are varied in a staggered manner. Example modalities and arrangements of modalities to produce variable bending stiffness profiles will now be described with reference to FIGS. 16C and 16D.

FIG. 16C is a cross-sectional view of the elongated shaft 106 of medical instrument 100 including a multi-modality construction configured to provide a variable bending stiffness profile 102 as shown, for example, in FIG. 16C. The multi-modality construction of the medical instrument 100 can comprise a plurality of layers. For example, as illustrated, the medical instrument 100 comprises an inner layer 144 and an outer layer 146. The inner and outer layers 144, 146 can surround various other features that enable some of the functionality of the medical instrument 100. For example, as illustrated in FIGS. 16A-16D, the medical instrument 100 is configured as a scope (e.g., endoscope, bronchoscope, ureteroscope, vascular scope, etc.). The scope can include, for example, a camera 136, one or more light sources 138, position sensors 140 (e.g., EM coils), and a working channel 142 as shown.

The multi-modality construction of the elongated shaft 106 can include a plurality of modalities or properties. As used in this context, modality or property refers to a material or method of manufacture that can be varied in different regions along the length of the elongated shaft 106 to produce a variable bending stiffness profile. Examples will now be described with reference to the inner and outer layers 144, 146 of the elongated shaft 106 of FIG. 16C, although those of ordinary skill in the art will appreciate that other modalities and properties can also be used in the construction of a medical instrument with a variable bending stiffness.

For example, the mechanical properties of each section of the elongated shaft 106 can be modulated using the two-layer construction of FIG. 16C. In this embodiment, the inner layer 144 comprises an endoskeleton 150. As described below and shown in FIG. 17, the endoskeleton 150 can comprise a laser cut hypotube made from a metal, such as nitinol or stainless steel. The material can vary depending on where in the elongated shaft 106 it is located. In some embodiments, the outer layer 146 can be a braided jacket. The braided jacket can include a braid 152 including the pull wire lumens and pull wires 108 and a thermoplastic material 154, which can be melted into a composite structure. As discussed below, various properties of the braided jacket can be modulated in different regions of the elongated shaft to produce different bending stiffnesses. In some embodiments, the inner and outer layers 144, 146 can be reversed (e.g., the endoskeleton 150 can be located in an outer layer).

As shown in FIG. 16C, the inner layer 144 and the outer layer 146 can be separated by a liner 148. The liner 148 can be configured to keep the thermoplastic material 154 from the braided jacket from flowing into endoskeleton 150 during reflow operations during manufacturing and can allow the endoskeleton 150 to move freely under the braided jacket when in use.

The endoskeleton 150 can be one modality that can be varied to develop a variable bending stiffness profile. For example, features of the endoskeleton 150 can be varied along its length to produce different bending stiffnesses in different regions of the elongated shaft 106. In some embodiments, the endoskeleton 150 provides hoop strength and kink resistance for the elongated shaft 106.

The endoskeleton 150 can be formed, in some embodiments, of either nitinol or stainless steel, although other materials may also be used. In some embodiments, the endoskeleton 150 can be formed in part of nitinol and in another part of stainless steel. In some embodiments, the active bending section 114 of the elongated shaft 106 uses a nitinol flexure design, which allows it to go through tight bends. An example endoskeleton 150 including a nitinol flexure design 156 in the active bending section 114 is shown in FIG. 17. The nitinol flexure design 156 can include various cut patterns designed to provide high axial stiffness to resist shrinkage during pull wire loads and low bending stiffness to reduce the force required to articulate the elongated shaft 106. In some embodiments, use of a nitinol material may be advantageous in this section because of the high strain and tight bends this section experiences during use. The super elastic properties of nitinol allow it to spring back into a straight configuration even when highly articulated and resist fatigue even after many articulations.

In some embodiments, the remainder of the endoskeleton 150 (e.g., the passive bending section 116, the internal shaft section 118, and the external shaft section 120) can be formed of stainless steel, for example. In some sections (e.g., the passive bending section 116, the internal shaft section 118), the stainless steel can be laser cut with different pitches, wherein the lower the pitch, the lower the bending stiffness (and greater the flexibility). An example of this is shown, for example, by sections 158, 160 of the endoskeleton 150 of FIG. 17. In some embodiments, the laser cut sections may exhibit low axial stiffness, and a stiffer braided jacket in these sections can be used to increase bending stiffness. In the external shaft section 120, the endoskeleton 150 can, in some embodiments, transition into a rigid hypotube, as illustrated by section 162 in FIG. 17. This can provide the medical instrument 100 with maximum axial and bending stiffness in this area and prevent the elongated shaft 106 from buckling since this portion of the scope will often be unsupported outside of the sheath.

In some embodiments, the elongated shaft 106 can include an endoskeleton 150 that advantageously provides an omni-directional or uniform bending stiffness circumferentially. The term omni-directional indicates that the elongated shaft 106 can have a bending stiffness that is the same in multiple directions. In some embodiments, the bending stiffness varies within 2-10 percent about any direction of bending. The advantage of an omni-directional or uniform bending stiffness is that the performance of the elongated shaft 106 is indifferent to the orientation of the elongated shaft. In some embodiments, the elongated shaft 106 can have both two-way and one-way steering.

The endoskeleton 150 can provide various modalities that can be varied or modulated along the length of the elongated shaft to produce different bending stiffness in different sections. These modalities can include, for example, material, flexure design, laser cut, pitch, etc. These modalities can be varied along the length of the endoskeleton 150 to provide different bending stiffness in different regions or sections.

The outer layer 146 can also include various modalities that can be varied or modulated along the length of the elongated shaft 106 to produce different bending stiffness in different sections. As noted previously, the outer layer 146 can comprise a braided jacket. In some embodiments, the braided jacket can be designed to house the pull wires 108 used for articulation of the bending section, provide mechanical structure and stability to the medical instrument, and seal the internals of the scope from the external environment.

The braided jacket can include a jacket material 154 and braid 152, with the pull wires 108 extending therethrough. In some embodiments, the braided jacket can provide mechanical structure and stability to the medical instrument 100. The braided jacket can have a number of parameters that can be modulated to affect the properties of the elongated shaft 106. For example, the jacket material 154 of the braided jacket can have a particular durometer or hardness. Different materials of different durometers can be used in different sections to produce different bending stiffnesses. In addition, the braids 152 of the braided jacket can be manufactured with a particular geometry or braid angle. The geometry and braid angle can be varied along the length of the elongated shaft 106 to produce different bending stiffnesses.

In the illustrated embodiment, the mechanical properties of the braided jacket can be modulated by adjusting one or more of the following modalities: the durometer of the jacket material 154, the braid 152 geometry, and the braid pic count (i.e., the braid angle). In general, lower durometer materials provide lower bending stiffness and higher durometer materials provide higher bending stiffness. Example materials that can be used for the braided jacket include polyether block amide (e.g., Pebax), available in a range of durometers from 25-72 D, and Nylon 12, which may be stiffer than Pebax. Other materials, such as plastics, can also be used. Regarding braid geometry, it is possible to adjust the shape and number of braids used in the braid layer. Those of skill in the art will appreciate that many different braid configurations possible. Finally, braid pic count (braid angle) can also be modulated. In some embodiments, the braided jacket may comprise additional modalities that can also be adjusted.

The above described modalities are provided by way of example only. Other modalities may also be used, either in place of or in addition to the described modalities, to create the variable bending stiffness profile of the medical instrument 100.

FIG. 16D schematically illustrates how various modalities can be modulated, according to one embodiment, in the multi-layer construction of the medical instrument 100 to create the bending stiffness profile 102 shown in FIG. 16B. For reference, a side view of the medical instrument 100 is shown in FIG. 16D, and the active bending section 114, the passive bending section 116, the internal shaft section 118, and the external shaft section 120 are illustrated, as well as the first bending stiffness zone 122 of substantially constant bending stiffness, the first transition zone 124, the second bending stiffness zone 126 of substantially constant bending stiffness, the second transition zone 128, the third bending stiffness zone 130 of substantially constant bending stiffness, the third transition zone 132, and the fourth bending stiffness zone 134 of substantially constant bending stiffness.

In the illustrated embodiment, first and second layers of the medical instrument 100 are represented schematically. The first layer can be, for example, the inner layer 144 described above, and the second layer can be, for example, the outer layer 146. As represented by the different cross-hatching, a modality of the first layer changes along the length of the elongated shaft 106 between the distal end 112 and the proximal end 110. In the illustrated example, the modality of the first layer comprises four distinct sections. Each of these sections can have a different property that makes a different contribution to the overall bending stiffness of the medical instrument 100. As one example, the first layer can comprise the endoskeleton 150 and the four distinct sections of the first layer can represent the four sections 156, 158, 160, 162 shown in FIG. 17. As shown in FIG. 16D, transitions between the four sections of the first layer generally occur within transitions zones 124, 128, 132.

In the illustrated embodiment, the second layer includes three different modalities. In some embodiments, the second layer can be a braided jacket, and the three modalities can represent the jacket material, braid geometry, and braid pic count as discussed above. In the illustrated example, the first modality includes four distinct sections. Each section can represent, for example, a material of different durometer or hardness. In the illustrated example, the second modality includes four distinct sections. Each section can represent, for example, a section with a different braid geometry. In the illustrated example, the third modality includes six distinct sections. Each section can represent, for example, a section of different pic count. In general, transitions between sections occur within transition zones 124, 128, 132, although as shown, for example, in the second and third modalities, this need not always be the case.

Together the arrangement of different sections of the various modalities of the first and second layer define the bending stiffness of the elongated shaft 106 of the medical instrument 100. In some embodiments, to achieve bending stiffness zones having a substantially constant bending stiffness (e.g., bending stiffness zones 122, 126, 130, 134), the transitions between the different sections of the various modalities of the first and second layer generally do not occur or are limited within the bending stiffness zones 122, 126, 130, 134. Because the construction of the elongated shaft 106 generally remains constant in these bending stiffness zones, the bending over the length of these zones can be substantially constant. In some embodiments, no transition between different sections of the various modalities of the first and second layer occurs within a bending stiffness zone of substantially constant bending stiffness. In some embodiments, at most one, two, or three transitions between different sections of the various modalities of the first and second layer occur within a bending stiffness zone of substantially constant bending stiffness.

In some embodiments, to achieve transition zones having a length over which the bending stiffness of the zone gradually transitions from a first bending stiffness to a second bending stiffness (e.g., transition zones 124, 128, 132), transitions between the different sections of the various modalities of the first and second layer generally occur within the transition zone. For example, in some embodiments, at least one, two, three, four, five, six, or more transitions between the different sections of the various modalities of the first and second layer generally occur within a transition zone. Additionally, to create a gradual (e.g., sloped or ramped) transition within a transition zone, the transitions between the different sections of the various modalities of the first and second layer can be generally staggered. That is, within a transition zone, transitions between the different sections of the various modalities of the first and second layer generally occur within the zone generally do not occur at the same point along the length of the elongated shaft 106. This can have a smoothing effect on the overall bending stiffness profile 102 of the medical instrument 100 within the transition zones 124, 128, 132. In some embodiments, at least two, three, four, five, six, or more transitions between the different sections of the various modalities of the first and second layer are staggered within each transition zone.

FIG. 16D illustrates that in some embodiments, the medical instrument 100 can comprise a multi-layer construction. Some layers may comprise a single modality (e.g., the first layer) and some layers may comprise a plurality of modalities (e.g., the second layer). In some embodiments, the medical instrument may comprise only a single layer. In some embodiments, the medical instrument may comprise more than two layers. Further, the illustrated modalities and transitions between sections illustrated in FIG. 16D are provided by way of example only. Those of skill in the art will readily appreciate that other arrangements are possible to produce various bending stiffness profiles as desired.

Figure 18A:
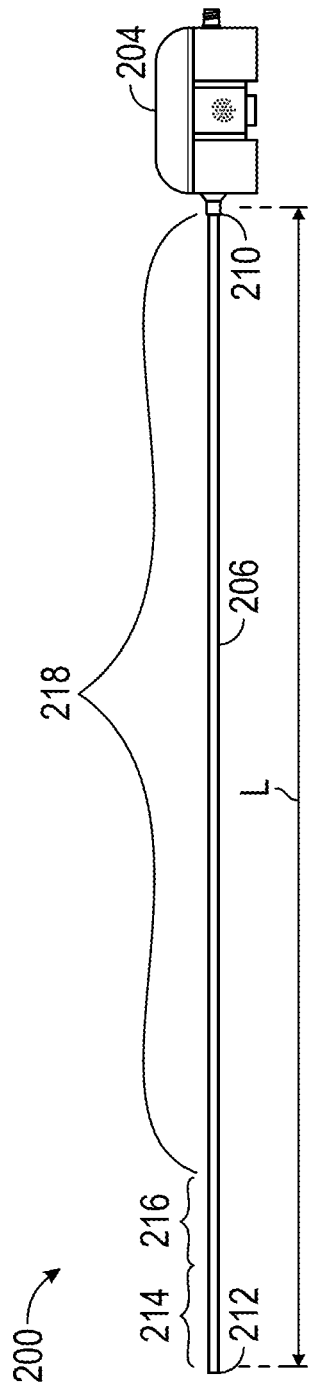
FIG. 18A is a side view of an embodiment of a medical instrument configured as a sheath and having a variable bending stiffness profile.
Figure 18B:
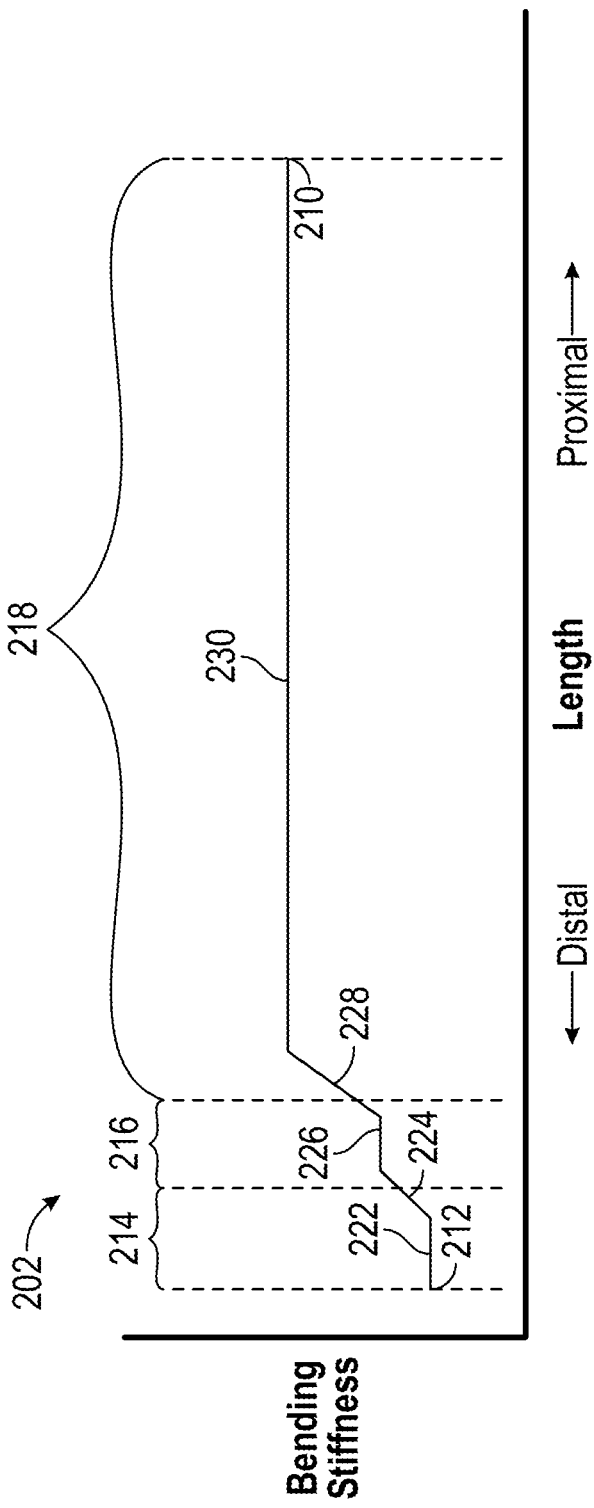
FIG. 18B illustrates an example variable bending stiffness profile of the medical instrument of FIG. 18A.
Figure 18C:
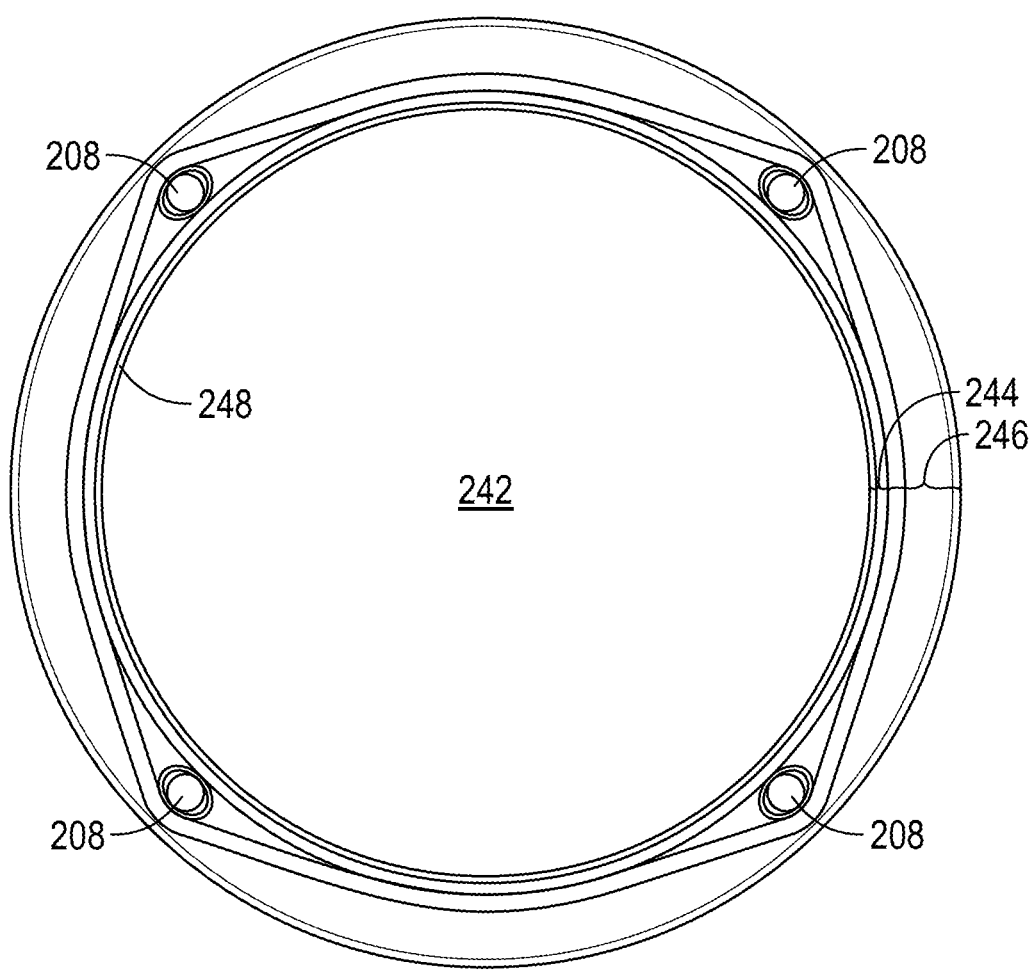
FIG. 18C illustrates a cross-sectional view of the medical instrument of FIG. 18A, showing an example multi-modality construction thereof.
Figure 18D:
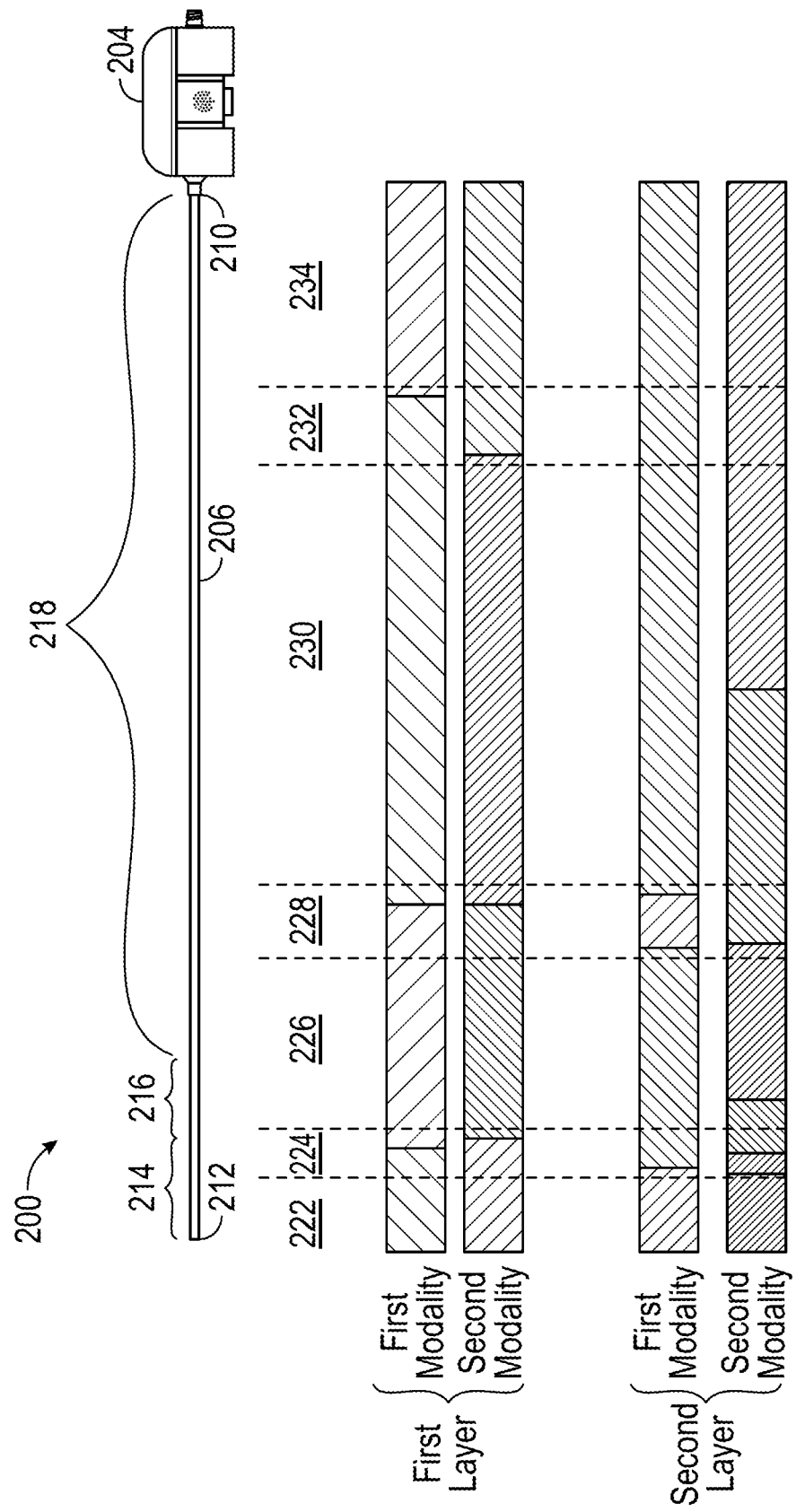
FIG. 18D schematically illustrates an example of how individual modalities of the multi-modal construction can be varied to achieve the representative variable bending stiffness profile of FIG. 18B for the medical instrument of FIG. 18A.

FIGS. 18A-18D relate to an embodiment of another medical instrument 200 having an example variable bending stiffness profile 202. In the illustrated embodiment, the medical instrument 200 is configured as a sheath. As will be described below, in some embodiments, the medical instrument 200 (sheath) can be used with the medical instrument 100 (scope) to form a compound structure, and relative movement of the medical instrument 200 (sheath) and the medical instrument 100 (scope) can be used to modulate the bending stiffness profile of the compound structure. FIG. 18A is a side view of the medical instrument 200. FIG. 18B illustrates the variable bending stiffness profile 202 of the medical instrument 200. FIG. 18C illustrates a cross-sectional view of the medical instrument 200, showing an example multi-modality construction thereof. FIG. 18D schematically illustrates an example of how the individual modalities of the multi-modal construction can be varied to achieve the variable bending stiffness profile 202 of the medical instrument 200.

In many respects, the medical instrument 200 is similar to the medical instrument 100. As illustrated in FIG. 18A, the medical instrument 200 includes an instrument base 204 and an elongated shaft 206. The elongated shaft 206 can extend between a proximal end 210 and a distal end 212. The proximal end 210 can extend from and be attached to the instrument base 204. The distal end 212 can be the leading end of the elongated shaft 206 of the medical instrument 200. The elongated shaft 206 includes a length L measured between the proximal end 210 and the distal end 212. In some embodiments, the length L of the medical instrument 200 (sheath) is less than the length L of the medical instrument 100 (scope), while in other embodiments, the length L of the medical instrument 200 (sheath) is equal to or greater than the medical instrument 100 (scope). In some embodiments, the length L of the medical instrument 200 (sheath) is about 50-300 mm less than the length L of the medical instrument 100 (scope). In some embodiments, the length L of the medical instrument 200 (sheath) is about 100 mm, about 150 mm, about 200 mm, about 250 mm, or about 300 mm less than the length L of the medical instrument 100 (scope). In some embodiments, the length L of the medical instrument 200 (sheath) is about 60%, about 70%, about 80%, or about 90% the length L of the medical instrument 100 (scope). In some embodiments, for example, the length L of the medical instrument 200 may be between about 600 and about 750 mm. In one example, the length L is about 680 mm.

In the illustrated embodiment, the elongated shaft 206 includes three different sections: a bending section 214 (also referred to an active bending section), a passive bending section 216, and an internal shaft section 218 (also referred to as a tracking section). The sections can be arranged serially along the length L of the elongated shaft 206 between the distal end 212 and the proximal end 210. Although three sections are illustrated, in some embodiments, a medical instrument can include more of less sections. For example, a medical instrument can include one, two, three, four, five, six, seven, or more sections.

Similar to the medical instrument 100, each section of the medical instrument 200 can be configured to provide a different function to facilitate the medical procedure and/or improve the drivability and control of the medical instrument 200. For example, in some embodiments, more distally located sections are more flexible to facilitate maneuverability of the elongated shaft 206, and more proximally located sections are stiffer to provide pushability of the elongated shaft 206, while preventing or reducing the likelihood of buckling. In some embodiments, the active bending section 214 provides steerability to the distal end of the medical instrument 200. In some embodiments, the passive bending section 216 provides enough flexibility to track up in to the upper lobes of the lung, for example, in the case of the bronchoscopy. In some embodiments, the internal shaft section 218 is flexible enough to be inserted through an introducer and tube bends, but pushable/rigid enough to provide support for the elongated shaft 206. In some embodiments, to achieve these different functions, each section comprises different bending stiffness characteristics or properties.

In some embodiments, the active bending section 214 has a length between about 50 mm and 80 mm, or approximately 65 mm. In some embodiments, the passive bending section 216 has a length between about 45 mm and 75 mm, or approximately 60 mm. In some embodiments, the internal shaft section 218 can have a length between about 410-500 mm, or approximately 450 for the internal zone. Advantageously, the different lengths of the three different zones are designed to desirably align the elongated shaft 206 with portions of the underlying scope, thereby creating a compound structure with desired variable stiffnesses along different lengths. In some embodiments, the lengths of one, more, or all of these sections can be different than the listed values.

FIG. 18B illustrates a representative bending stiffness profile 202 of the elongated shaft 206 of the medical instrument 200. In the illustrated embodiment and as seen in the example bending stiffness profile 202, the elongated shaft 206 of the medical instrument 200 includes three bending stiffness zones of substantially constant bending stiffness and two transition zones, with each transition zone positioned between a pair of adjacent bending stiffness zones. In the illustrated example, the medical instrument 200 includes (arranged distally to proximally) a first bending stiffness zone 222 of substantially constant bending stiffness, a first transition zone 224, a second bending stiffness zone 226 of substantially constant bending stiffness, a second transition zone 228, and a third bending stiffness zone 230 of substantially constant bending stiffness.

Although three bending stiffness zones and two transition zones are shown and described, other embodiments may include other numbers of bending stiffness zones and transmissions For example, a medical instrument could include two, three, four, five, six, or more bending stiffness zones of substantially constant bending stiffness, separated by one, two, three, four, five, or more transition zones.

In the illustrated embodiment, the first bending stiffness zone 222 has the lowest substantially constant bending stiffness, the second bending stiffness zone 226 has a substantially constant bending stiffness that is higher than that of the first bending stiffness zone 222, and the third bending stiffness zone 230 has a substantially constant bending stiffness that is higher than that of the second bending stiffness zone 226. Thus, the bending stiffness of the medical instrument 200 generally increases from the distal end 212 to the proximal end 210. This need not be the case in all embodiments. For example, the bending stiffness could increase, decrease, and then increase again or generally decrease.

Further, in the illustrated embodiment, the transition zones 224, 228 include generally or substantially constant slopes. It will be appreciated that the slope of each transition zone can vary. For example, the slope of the first transition zone 224 can be less than the slope of the second transition zone 228. Again, this need not be the case in all embodiments.

For reference, FIG. 18B also illustrates how, in one example, the bending stiffness profile 202 aligns with the bending section 214, the passive bending section 216, and the internal shaft section 218. In the illustrated embodiment, each section includes one bending stiffness zone of substantially constant bending stiffness. For example, the first bending stiffness zone 222 is positioned in the bending section 214, the second bending stiffness zone 226 is positioned in the passive bending section 216, and the third bending stiffness zone 230 is positioned in the internal shaft section 218. The elongated shaft 206 can be configured such that the substantially constant bending stiffness of the bending stiffness zone positioned within the section facilitates or enables the section to perform its specified function. The transition zones 224, 228 provide lengths over which the bending stiffness of the elongated shaft can gradually vary from a lower value to a higher value (or vice versa). As before, having regions where the bending stiffness varies gradually (as opposed to abruptly) can help to avoid stress risers and failure points within the elongated shaft 206.

In the illustrated embodiment, the transition zones 224, 228 are positioned to overlap adjacent sections. For example, the first transition zone 224 is positioned between and partially overlaps the bending section 214 and the passive bending section 216. The second transition zone 228 is positioned between and partially overlaps the passive bending section 216 and the internal shaft section 218. Other arrangements and positions for the transition zones are also possible. For example, a transition zone could be positioned entirely within one section, for example, at a distal end of the section, at a proximal end of the section, or along the length of a section between the proximal and distal ends.

FIG. 18C is a cross-sectional view of the elongated shaft 206 of medical instrument 200 including a multi-modal construction configured to provide a variable bending stiffness profile 202 as shown, for example, in FIG. 18C. The multi-modal construction of the medical instrument 200 can comprise a plurality of layers. For example, as illustrated, the medical instrument 200 comprises an inner layer 244 and an outer layer 246. The inner and outer layers 244, 246 can surround a working or inner channel 242 as shown. The inner channel 242 can be configured in size and shape to receive a scope (e.g., the medical instrument 100) therein. In some embodiments, the scope can telescope through the inner channel 242. A liner 248 can be provided around the inner channel 242. The liner 248 can be configured to allow the first medical instrument 100 to move freely through the inner channel 242 during use.

In the illustrated embodiment, both the inner layer 244 and the outer layer 246 can comprise a braided jacket. The braided jacket can include a braid made from a thermoplastic material. In some embodiments one of the inner layer 244 and the outer layer 246 includes pull wires 208. As discussed above, various properties of the braided jacket can be modulated in different regions of the elongated shaft to produce different bending stiffnesses. For example, in each layer 244, 246, braid material (durometer), braid geometry, and braid pic count can be modulated to produce different bending stiffnesses. Other modalities may also be used, either in place of or in addition to the described modalities, to create the variable bending stiffness profile of the medical instrument 200.

FIG. 18D schematically illustrates how the various modalities can be modulated, according to one embodiment, in the multi-layer construction of the medical instrument 200 to create the bending stiffness profile 202 shown in FIG. 18B. For reference, a side view of the medical instrument 200 is shown in FIG. 18D, and the active bending section 214, the passive bending section 216, and the internal shaft section 218 are illustrated, as well as the first bending stiffness zone 222 of substantially constant bending stiffness, the first transition zone 224, the second bending stiffness zone 226 of substantially constant bending stiffness, the second transition zone 228, and the third bending stiffness zone 230 of substantially constant bending stiffness.

In the illustrated embodiment, first and second layers of the medical instrument 200 are represented schematically. The first layer can represent the inner layer 244 and the second layer can represent the outer layer 246, which, as described above, can both be braided jackets. As illustrated in FIG. 18D, both the first layer and the second layer can include at least two different modalities. In the illustrated example, the first modality of the first layer includes four distinct sections, and the second modality of the first layer includes four distinct sections. In the illustrated example, the first modality of the second layer includes four distinct sections, and the second modality of the second layer includes six distinct sections. As with the medical instrument 100, in general, transitions between sections do not occur or are limited in bending zones 222, 226, 230 of substantially constant bending stiffness, and transitions between sections occur within transition zones 224, 228, although this need not always be the case. Other numbers of layers, having different numbers of modalities and different numbers of sections can be used.

B. Modulating Bending Stiffness Profiles.

As mentioned briefly above, in some embodiments, a compound structure (sometimes referred to as a medical instrument) can comprise a scope (e.g., the medical instrument 100) positioned within an inner channel of a sheath (e.g., the medical instrument 200). As noted above, the term "compound structure" can refer to and encompass all parts of the scope and the sheath whenever the scope is positioned within the inner channel of the sheath, including parts of the scope that may extend distally from the sheath, or parts of the sheath that may extend distally from the scope. One or both of the scope and sheath can comprise a variable bending stiffness profile (see, e.g., FIGS. 16B and 18B) as described above. The compound structure can comprise a variable bending stiffness profile that is a combination of the individual variable bending stiffness profiles of the scope and sheath. Further, the variable bending stiffness profile of the compound structure can be modulated, changed, or varied by adjusting the relative positions of the scope and the sheath. In some embodiments, modulation of the variable bending stiffness profile of the compound structure can occur during a medical procedure (e.g., intraoperatively), either manually or robotically, so as to facilitate the medical procedure.

FIG. 19A illustrates a medical instrument or compound structure 300. The compound structure 300 includes a scope 100, for example, the medical instrument 100 of FIGS. 16A-16D, positioned within the inner channel of a sheath 200, for example, the medical instrument 200 of FIGS. 18A-18D. Specifically, the elongated shaft 106 of the scope 100 can extend through the inner channel 242 of the elongated shaft 206 of the sheath 200. In some embodiments, the scope 100 and the sheath 200 are coaxial. In the illustrated embodiment of FIG. 19A, the scope 100 and the sheath 200 are positioned relative to each other such that the distal end 112 of the scope 100 is aligned with the distal end 212 of the sheath 200.

While the scope 100 and the sheath 200 may be coaxial, they can be independently controlled relative to one another. For example, the scope 100 includes an instrument base 104 that can be attached to an instrument drive mechanism on a first robotic arm. The first robotic arm can move the instrument base 104 to insert or retract the scope 100 in the directions 107. Similarly, the sheath 200 includes an instrument base 204 that can be attached to an instrument drive mechanism on a second robotic arm. The second robotic arm can move the instrument base 204 to insert or retract the sheath 200 in the directions 207. Movement of the scope in the directions 107 can be independent of movement of the sheath 200 in the directions 207. In some embodiments, the scope 100 and the sheath 200 are not be coextensive in length, such that one (typically the sheath 200) will be shorter than the other (typically the scope 100).

Figure 19B:
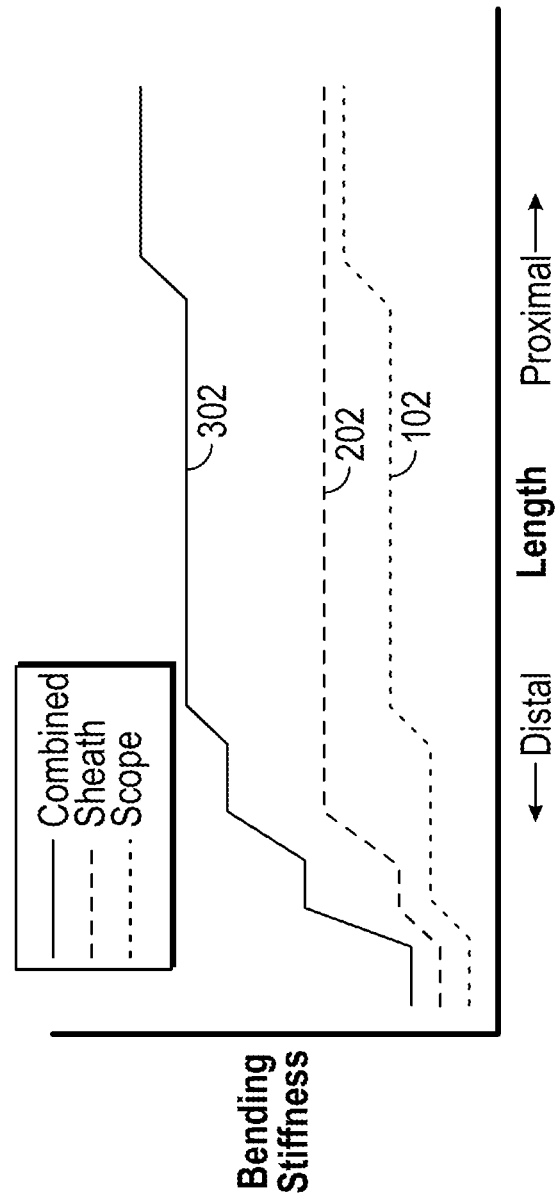
FIG. 19B illustrates example bending stiffness profiles for the scope, the sheath, and the compound structure of FIG. 19A.
Figure 19C:
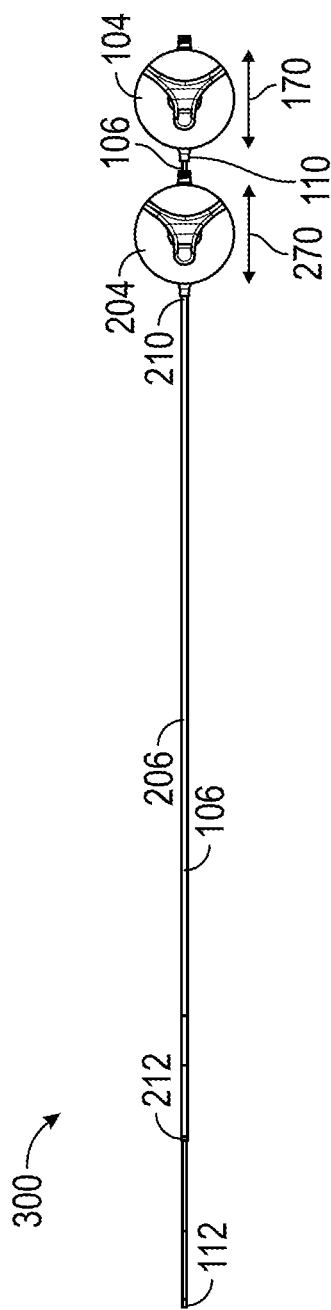
FIG. 19C illustrates a top view of an embodiment of the compound structure of FIG. 19A with the distal end of the scope extended beyond the distal end of the sheath.

FIG. 19B illustrates example bending stiffness profiles 102, 202, 302 of the scope 100, the sheath 200, and the compound structure 300, respectively. The scope 100 may comprise a variable bending stiffness profile 102 as described above (see, e.g., FIG. 16B). In the illustrated example, the bending stiffness profile 102 of the scope 100 includes four bending stiffness zones of substantially constant bending stiffness and three transition zones. The sheath 200 may also comprise a variable bending stiffness profile 202 as described above (see, e.g., FIG. 18B). In the illustrated example, the bending stiffness profile 202 of the sheath 200 includes three bending stiffness zones of substantially constant bending stiffness and two transition zones.

As shown in FIG. 19B, the compound structure 300 includes a bending stiffness profile 302 that is based on the bending stiffness profiles 102, 202 of the scope 100 and the sheath 200. In the illustrated embodiment, the bending stiffness profile 302 includes five bending stiffness zones of substantially constant bending stiffness and four transition zones. Thus, in some embodiments, the bending stiffness profile 302 of the compound structure 300 comprises more bending stiffness zones of substantially constant bending stiffness and/or more transition zones than one or both the bending stiffness profiles 102, 202 of the scope 100 and the sheath 200. In some embodiments, the bending stiffness profile 302 of the compound structure 300 comprises the same number of bending stiffness zones of substantially constant bending stiffness and/or more transition zones as one or both the bending stiffness profiles 102, 202 of the scope 100 and the sheath 200.

For example, if the scope 100 comprises n bending stiffness zones, the compound structure 300 can, in some embodiments, comprise any number of bending stiffness zones between n+1 and 2n (inclusive) or more. As another example, if the sheath 200 comprises m bending stiffness zones, the compound structure 300 can, in some embodiments, comprise any number of bending stiffness zones between m+1 and 2m (inclusive) or more. As an additional example, if the scope comprises n bending stiffness zones and the sheath 200 comprises m bending stiffness zones, the compound structure 300 can, in some embodiments, comprise any number of bending stiffness zones between n+m+1 and 2(n+m) (inclusive) or more.

Further, the bending stiffness profile 302 of the compound structure 300 can be modulated, changed, or varied, by adjusting the relative positions of the scope 100 and sheath 200. FIG. 19C illustrates an example, where the position of the scope 100 has been adjusted relative to the sheath 200. Specifically, in the illustrated example, the distal end 112 of the scope 100 has been positioned beyond (more distal of) the distal end 212 of the sheath 200. This can be accomplished, for example, by advancing the scope 100, retracting the sheath 200, or performing a combination thereof.

Figure 19D:
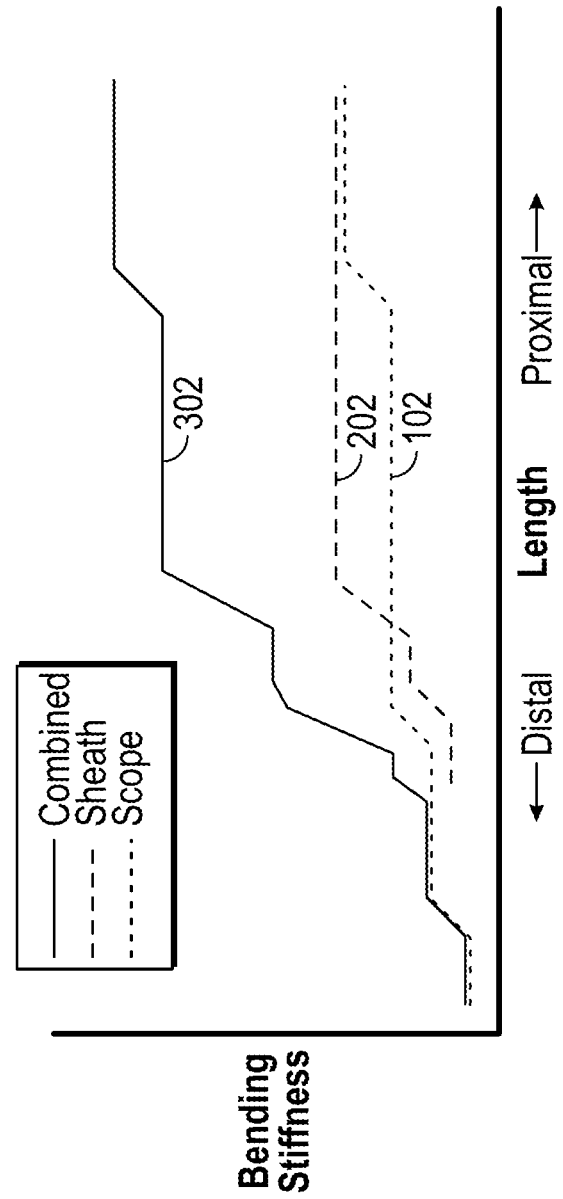
FIG. 19D illustrates example bending stiffness profiles for the scope, the sheath, and the compound structure of FIG. 19C.

FIG. 19D illustrates the bending stiffness profiles 102, 202, 302 of the scope 100, the sheath 200, and the compound structure 300, respectively, with the scope 100 and the sheath 200 positioned as shown in FIG. 19C. In the illustrated example, the bending stiffness profile 302 of the compound structure 300 comprises six bending stiffness zones of substantially constant bending stiffness separated by transition zones. Further, it should be appreciated that the bending stiffness profile 302 of FIG. 19D has been modulated or changed relative to the to the bending stiffness profile 302 of FIG. 19B. This is because, with the scope 100 and the sheath 200 in different positions, the bending stiffness profiles 102, 202 line up in a different way resulting in a different bending stiffness profile 302.

Thus, the compound structure 300 can advantageously modulate or change its bending stiffness profile 302 based on a plurality of relative positions of the scope 100 and the sheath 200, including relative positions where the distal end 112 of the scope 100 is positioned beyond the distal end 212 of the sheath 200, relative positions where the distal end 212 of the sheath 200 is positioned beyond the distal end 112 of the scope 100, and the relative position where the distal end 112 of the scope 100 is aligned with the distal end 212 of the sheath 200.

In some embodiments, moving the scope 100 relative to the sheath 200 (or vice versa) can result in a bending stiffness profile 302 of the compound structure that has more, fewer, or the same number of bending stiffness zones of substantially constant bending stiffness as prior to the movement.

In some embodiments, modulation of the scope 100 by the sheath 200 can occur only along a portion of the scope 100 that is positioned within the sheath 200, with the remainder of the scope 100 (e.g., the portion extending distally of the sheath 200) having its original bending stiffness profile, as shown in FIG. 19D.

During a medical procedure, a physician and/or a robotically-enabled medical system can adjust the relative position of the scope 100 and the sheath 200 to modulate the bending stiffness profile 302 of the compound structure. This can be done to produce a bending stiffness profile 302 that is more suited for a particular maneuver to be performed. In some embodiments, this is performed manually. In some embodiments, this is performed automatically (e.g., as controlled by a processor or navigation system). In some embodiments, this is performed intraoperatively. This may advantageously allow use of different bending stiffness profiles during different instances of a procedure without needing to change medical instruments.

Figure 20A:
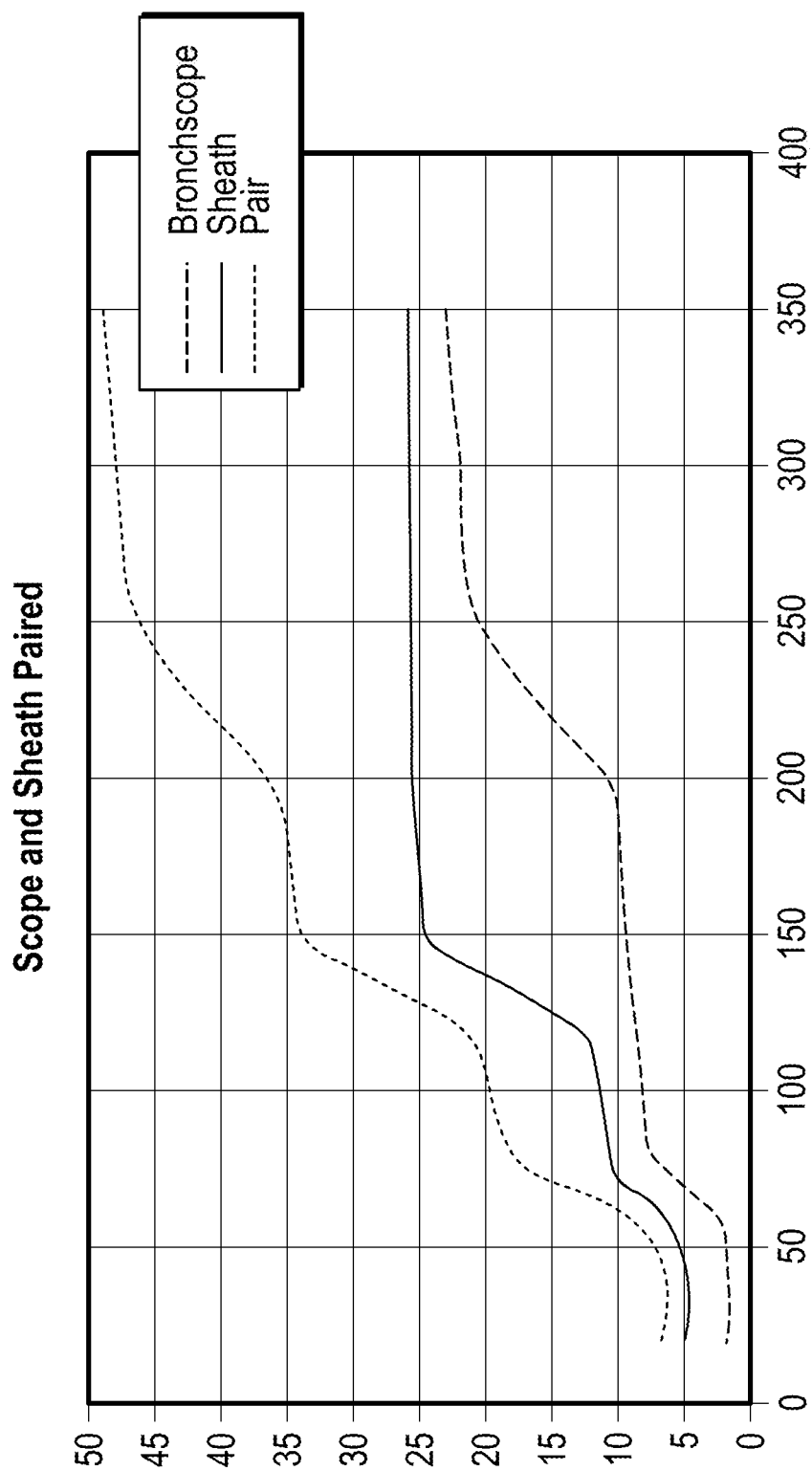
FIGS. 20A-20C present experimental data related to a first embodiment of a compound structure including a scope and sheath configured according to the principles described herein.
Figure 20B:
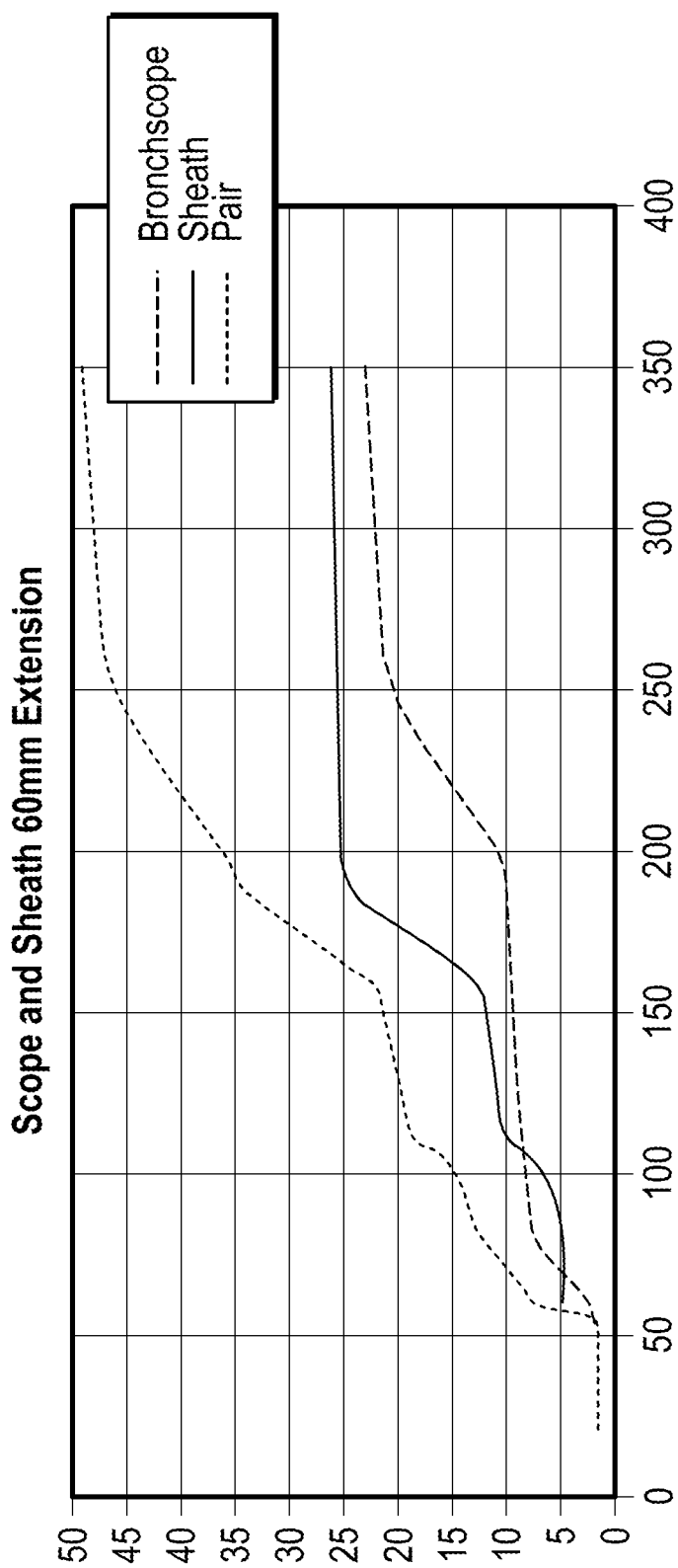
Figure 20C:
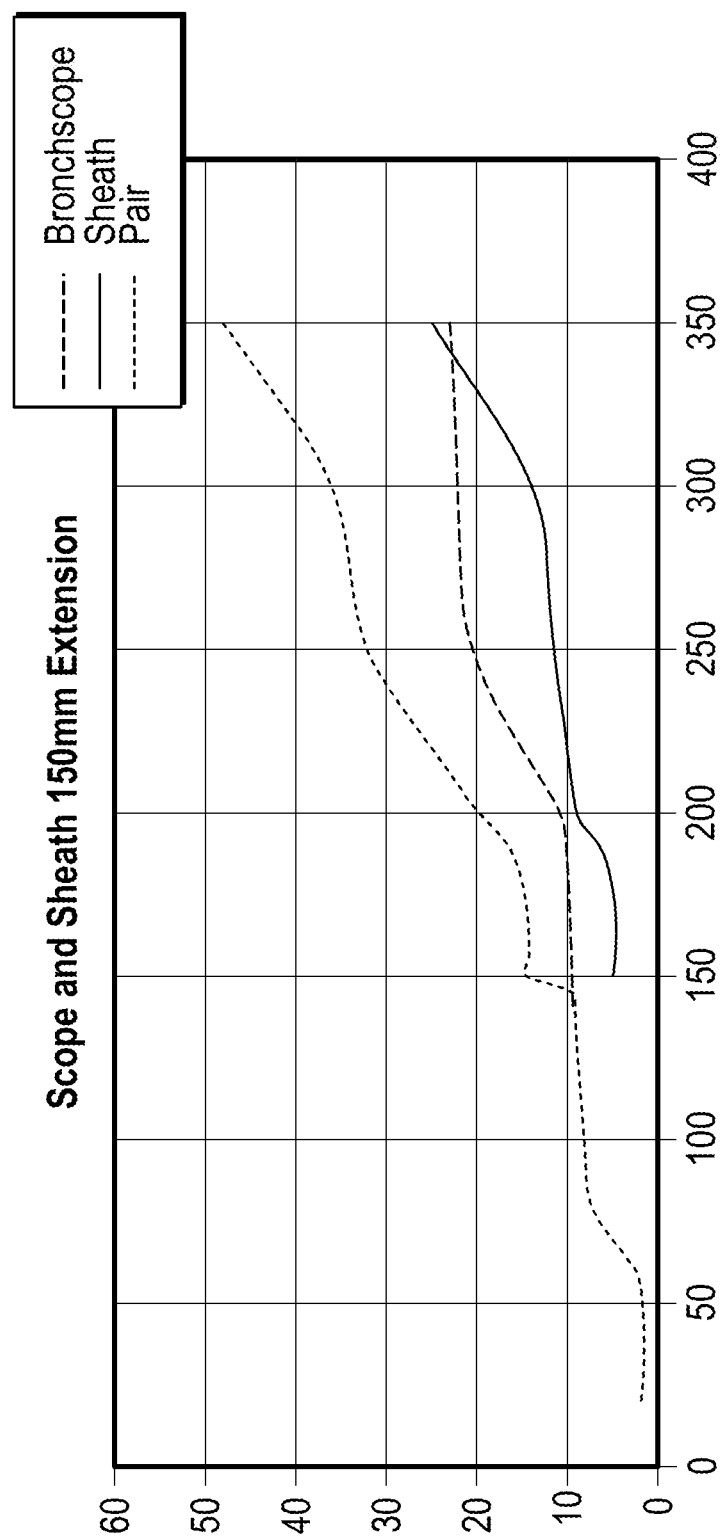

FIGS. 20A-20C present experimental data related to a first embodiment of a compound structure (scope and sheath) configured according to the principles described herein. In this example, both the scope and the sheath comprise a variable bending stiffness profile. FIG. 20A illustrates the bending stiffness profiles of the scope and sheath, as well as a combined bending stiffness profile of the compound structure when distal ends of the scope and sheath are aligned. FIG. 20B illustrates the bending stiffness profiles of the scope and sheath, as well as a combined bending stiffness profile of the compound structure when the distal end of the scope is extended 60 mm beyond the distal end of the sheath. FIG. 20C illustrates the bending stiffness profiles of the scope and sheath, as well as a combined bending stiffness profile of the compound structure when the distal end of the scope is extended 150 mm beyond the distal end of the sheath. Comparing the combined bending stiffness profiles of the compound structure shown in FIGS. 20A-20C it can be seen that the combined bending stiffness profile can be modulated by adjusting the relative position of the scope and the sheath.

Figure 21A:
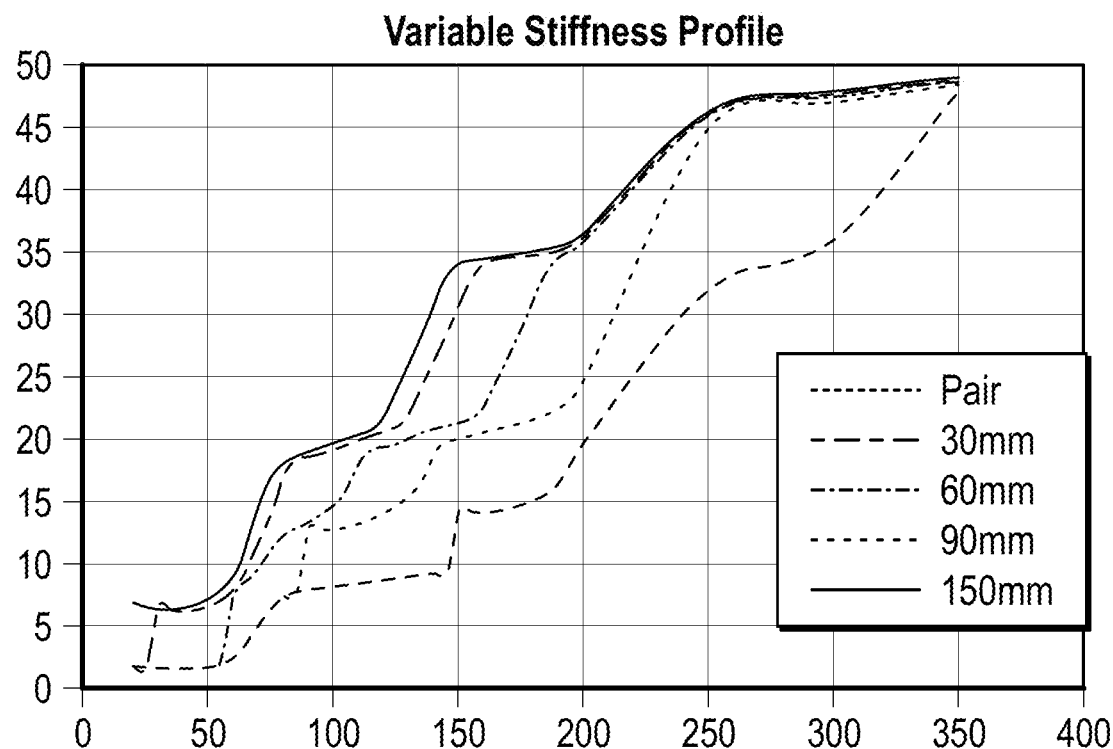
FIGS. 21A and 21B present experimental data related to a second embodiment of a compound structure including a scope and sheath configured according to the principles described herein.
Figure 21B:
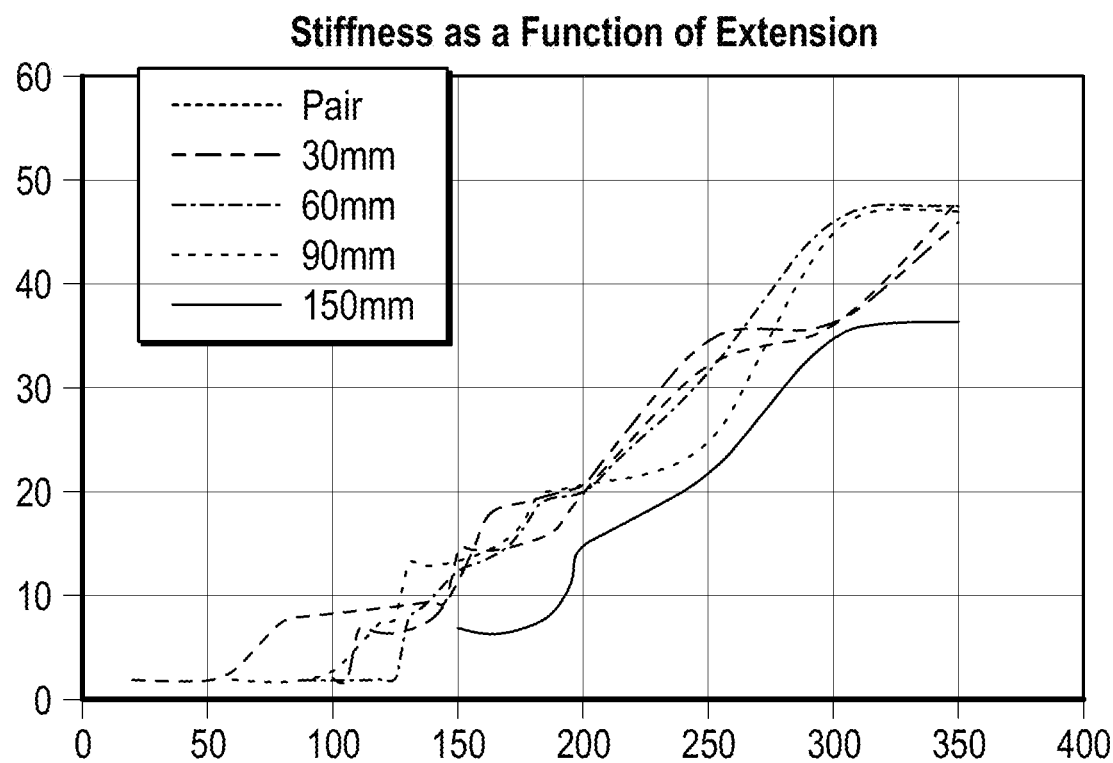

FIGS. 21A and 21B present experimental data related to a second embodiment of a compound structure (scope and sheath) configured according to the principles described herein. In this example, both the scope and the sheath comprise a variable bending stiffness profile. FIG. 21A illustrates variable stiffness profiles for the compound structure at different extensions of the scope relative to the sheath. As shown, all five variable stiffness profiles of the compound structure are different. FIG. 21B illustrates the variable stiffness profile of the compound structure as a function of extension of the scope relative to the sheath. Again, it is shown that adjusting the position of the scope relative to the sheath modulate the bending stiffness profile of the compound structure.

Figure 23:
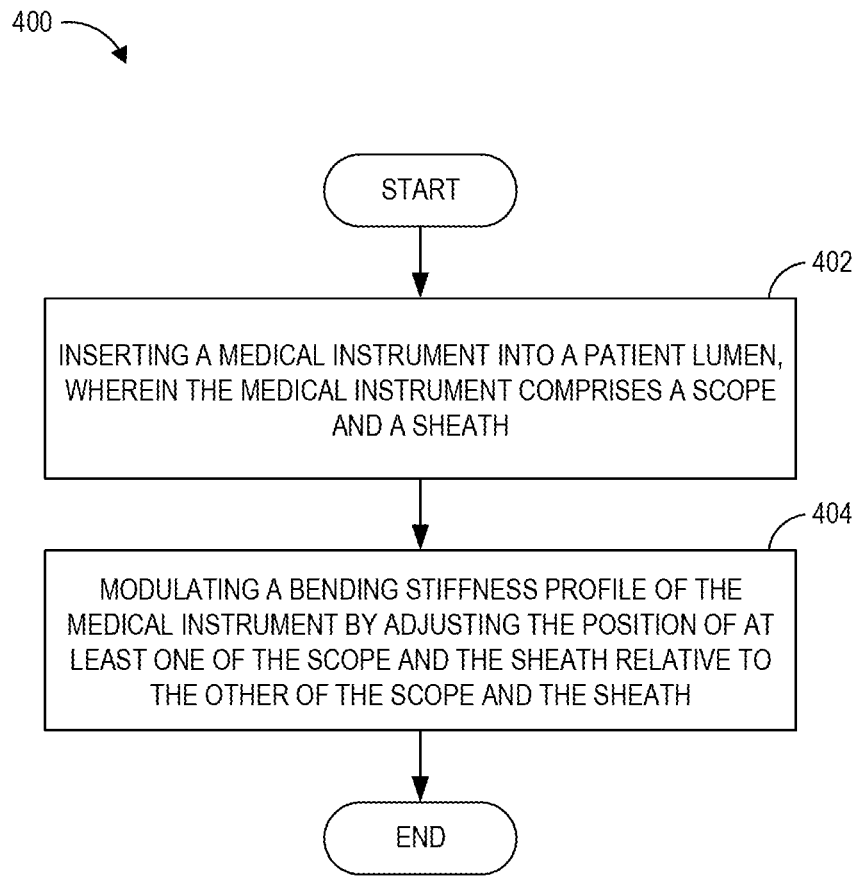
FIG. 23 is a flowchart illustrating an example method for navigating a medical instrument within a patient lumen.

FIG. 23 is a flowchart illustrating an example method 400 for navigating a medical instrument within a patient lumen. In some embodiments, the medical instrument may comprise a scope and sheath, such as the compound structure 300 described above. The method 400 can be implemented in a robotic medical system. In some embodiments, the method 400 can be implemented manually.

The method 400 begins at block 402. At block 402, the medical instrument is inserted into a patient lumen. The medical instrument may comprises a scope and sheath. The scope may comprise a plurality of bending stiffness zones arranged along a length of the scope. In some embodiment, each of the bending stiffness zones has a bending stiffness that is substantially uniform. The sheath may comprise a plurality of bending stiffness zones arranged along a length of the sheath and an inner channel. The scope can be positioned within the inner channel of the sheath. The patient lumen can comprise a bronchial airway, although the method 400 may be implemented for use with other patient lumens as well.

Next, at block 404, the bending stiffness profile of the medical instrument can be modulated by adjusting the position of at least one of the scope and the sheath relative to the other of the scope and the sheath. In some embodiments, modulating the bending stiffness profile of the medical instrument comprises at least one of advancing the scope and retracting the sheath such that the scope extends distally from the sheath. In some embodiments, modulating the bending stiffness profile of the medical instrument comprises at least one of advancing the sheath and retracting the scope such that a distal end of the scope is positioned within the inner channel of the sheath. In some embodiments, a distal end of the sheath can be positioned distally beyond the distal end of the scope. In some embodiments, the distal end of the scope is aligned with a distal end of the sheath.

In some embodiments, the scope comprises at least four bending stiffness zones, each having a substantially constant bending stiffness along a length of the bending stiffness zone. In some embodiments, the scope comprises at least three transition zones, each of the at least three transition zones positioned between a pair of the at least four bending stiffness zones. In some embodiments, the scope comprises at least three bending stiffness zones, each having a substantially constant bending stiffness along a length of the bending stiffness zone. In some embodiments, the scope comprises at least two transition zones, each of the at least two transition zones positioned between a pair of the at least three bending stiffness zones. In some embodiments, a first bending stiffness zone has a bending stiffness that is less than a bending stiffness of the other bending stiffness zones. In some embodiments, a third zone of bending stiffness extends through an introducer. In some embodiments, a fourth zone of bending stiffness does not extend through the patient lumen, nor through the introducer.

3. Implementing Systems and Terminology

Implementations disclosed herein provide systems, methods and apparatus for medical instruments with variable bending stiffness profiles.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The position estimation and robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the term "approximately" or "about" refers to a range of measurements of a length, thickness, a quantity, time period, or other measurable value. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical system comprising:
an elongated member having a length extending between a distal end and a proximal end, the elongated member further comprising n bending stiffness zones arranged along the length of the elongated member, wherein n is greater than or equal to two, wherein each of the n bending stiffness zones comprises a different bending stiffness, and wherein the bending stiffness of each of the n bending stiffness zones is substantially uniform along a length of the bending stiffness zone;
a sheath having a sheath length extending between a sheath distal end and a sheath proximal end, the sheath comprising an inner channel, the sheath further comprising m bending stiffness zones arranged along the length of the sheath, wherein m is greater than or equal to two, wherein each of the m bending stiffness zones comprises a different bending stiffness, and wherein the bending stiffness of each of the m bending stiffness zones is substantially uniform along a length of the bending stiffness zone;
a first drive mechanism configured to control movement of the elongated member independent of a movement of the elongated member; and
a second drive mechanism configured to control the movement of the sheath independent of the movement of the elongated member;
wherein the elongated member is configured to move within the inner channel of the sheath such that the elongated member and the sheath form a compound structure, wherein the compound structure comprises:
a first bending stiffness profile when the distal end of the elongated member is aligned with the sheath distal end, and
a second bending stiffness profile different than the first bending stiffness profile when the distal end of the elongated member extends beyond the sheath distal end,
wherein each of the first and second bending stiffness profiles comprise a plurality of bending stiffness zones; and wherein the medical system further comprises a processor configured to operate the first drive mechanism and the second drive mechanism to:
adjust a position of the elongated member within the inner channel of the sheath relative to the sheath to select between the first bending stiffness profile and the second bending stiffness profile based on an intended movement of the compound structure; and
move the compound structure.

2. The medical system of claim 1, wherein the compound structure comprises at least n+1 bending stiffness zones when the elongated member is advanced through the sheath such that the elongated member distal end is positioned distally of the sheath distal end.

3. The medical system of claim 1, wherein:
the n bending stiffness zones of the elongated member comprise at least three bending stiffness zones arranged along the length of the elongated member, each bending stiffness zone; and
the bending stiffness of each of the at least three bending stiffness zones is greater or less than the bending stiffness of an adjacent bending stiffness zone.

4. The medical system of claim 3, wherein the elongated member further comprises a braided jacket,
the elongated member further comprises at least two transition zones, each transition zone comprising a variable bending stiffness extending over a length of the transition zone between each pair of the at least three bending stiffness zones,
the variable bending stiffness of each transition zone varies from a first bending stiffness on a first side of the transition zone to a second bending stiffness on a second side of the transition zone, and
for at least one of the transition zones, the variable stiffness extending over the length of the zone is caused in part by:
changing a jacket material of the braided jacket from a first material having a first durometer to a second material having a second durometer at a first location along the transition zone,
changing a braid geometry of the braided jacket from a first braid geometry to a second braid geometry at a second location along the transition zone, the second location different from the first location, and
changing a braid pic count of the braided jacket from a first braid pic count to a second braid pic count at a third location along the transition zone, the third location different from the first and second locations.

5. The medical system of claim 4, wherein, for each transition zone, the variable bending stiffness varies from the first bending stiffness on the first side of the transition zone to the second bending stiffness on the second side of the transition zone with a substantially linear slope.

6. The medical system of claim 4, wherein the length of each of the transition zones is least 10 mm.

7. The medical system of claim 3, wherein the bending stiffness of the bending stiffness zone closest to the distal end is less than the bending stiffness of each of the two other bending stiffness zones.

8. The medical system of claim 7, wherein the bending stiffness of the bending stiffness zone closest to the proximal end is greater than the bending stiffness of each of the two other bending stiffness zones.

9. The medical system of claim 3, wherein the length of each of the bending stiffness zones is at least 50 mm.

10. The medical system of claim 1, wherein the elongated member comprises an inner layer and an outer layer.

11. The medical system of claim 10, wherein the outer layer comprises a braided jacket and the inner layer comprises an endoskeleton.

12. The medical system of claim 11, wherein the braided jacket comprises one or more pull wires extending therethrough.

13. The medical system of claim 11, wherein a bending stiffness of the elongated member in a transition zone comprising a variable bending stiffness extending over a length of the transition zone between a pair of the n bending stiffness zones is configured to be modulated by at least two of:
changing a jacket material of the braided jacket from a first material having a first durometer to a second material having a second durometer at a first location along the transition zone,
changing a braid geometry of the braided jacket from a first braid geometry to a second braid geometry at a second location along the transition zone, the second location different from the first location, and
changing a braid pic count of the braided jacket from a first braid pic count to a second braid pic count at a third location along the transition zone, the third location different from the first and second locations.

14. The medical system of claim 13, wherein the endoskeleton comprises a first portion formed of nitinol and a second portion formed of stainless steel, and wherein the bending stiffness of the transition zone is further configured to by modulated by changing endoskeleton from the first portion to the second portion at a fourth location along the transition zone, the fourth location different from the first, second, and third locations.

15. The medical system of claim 14, wherein the second portion of the endoskeleton further comprises a section formed as a rigid hypotube.

16. The medical system of claim 13, wherein the endoskeleton comprises a first section comprising coils having at least a first pitch and a second section comprising coils having at least a second pitch, and wherein the bending stiffness of the transition zone is further configured to by modulated by changing endoskeleton from the first section to the second section at a fourth location along the transition zone, the fourth location different from the first, second, and third locations.

17. The medical system of claim 1, wherein the elongated member comprises an endoscope.

18. The medical system of claim 1, wherein the elongated member comprises a bending stiffness profile that is omni-directional.

19. The medical system of claim 1, wherein the elongated member comprises a bending stiffness profile that is stepped.

20. The medical system of claim 1, wherein the elongated member comprises a multi-modal construction wherein a plurality of modalities change properties along the length of the elongated shaft to produce the n bending stiffness zones arranged along the length of the elongated member.

21. The medical system of claim 20, wherein: a transition zone is positioned between each pair of the n bending stiffness zones, each transition zone comprising a variable bending stiffness extending over a length of the transition zone, wherein the variable bending stiffness of each transition zone varies from a first bending stiffness on a first side of the transition zone to a second bending stiffness on a second side of the transition zone; and at least two of the plurality of modalities change properties within at least one transition zone.

22. The medical system of claim 21, wherein each of the at least two of the plurality of modalities that change properties within the at least on transition zone change properties at different locations along the length within the transition zone.

23. The medical system of claim 22, wherein the plurality of modalities comprise at least a plurality of: a jacket material durometer of a braided jacket of the elongated member; a braid geometry of the braided jacket of the elongated member; a braid pic count of the braided jacket of the elongated member; and a construction of an endoskeleton of the elongated member.

* * * * *

UNITED STATES PATENT AND TRADEMARK OFFICE
CERTIFICATE OF CORRECTION

| | |
|---|---|
| PATENT NO. | : 11,109,920 B2 |
| APPLICATION NO. | : 16/280300 |
| DATED | : September 7, 2021 |
| INVENTOR(S) | : Aadel Al-Jadda et al. |

It is certified that error appears in the above-identified patent and that said Letters Patent is hereby corrected as shown below:

In the Claims

Column 40, Line 50, Claim 1, "elongated member" should read --sheath--.

Column 42, Line 56, Claim 20, "elongated shaft" should read --elongated member--.

Signed and Sealed this
Fourteenth Day of June, 2022

Katherine Kelly Vidal
*Director of the United States Patent and Trademark Office*